United States Patent
Larsen et al.

(10) Patent No.: US 9,921,178 B2
(45) Date of Patent: Mar. 20, 2018

(54) ELECTROCHEMICAL SENSOR FOR SENSING NITROUS OXIDE

(71) Applicant: Unisense Environment A/S, Aarhus N (DK)

(72) Inventors: Lars Hauer Larsen, Hinnerup (DK); Michael Nielsen, Viby J (DK); Mikkel Holmen Andersen, Galten (DK)

(73) Assignee: Unisense Environment A/S, Aarhus N (DK)

( * ) Notice: Subject to any disclaimer, the term of this patent is extended or adjusted under 35 U.S.C. 154(b) by 197 days.

(21) Appl. No.: 14/655,709

(22) PCT Filed: Dec. 20, 2013

(86) PCT No.: PCT/DK2013/050454
§ 371 (c)(1),
(2) Date: Jun. 25, 2015

(87) PCT Pub. No.: WO2014/101921
PCT Pub. Date: Jul. 3, 2014

(65) Prior Publication Data
US 2015/0338370 A1  Nov. 26, 2015

(30) Foreign Application Priority Data

Dec. 28, 2012 (DK) .............................. 2012 00200 U
Dec. 28, 2012 (DK) ................................ 2012 70834

(51) Int. Cl.
*G01N 27/404* (2006.01)
*G01N 27/28* (2006.01)
*G01N 33/00* (2006.01)

(52) U.S. Cl.
CPC ....... *G01N 27/404* (2013.01); *G01N 27/4045* (2013.01); *G01N 33/0036* (2013.01); *G01N 33/0037* (2013.01); *G01N 27/283* (2013.01)

(58) Field of Classification Search
CPC ..................................................... G01N 27/404
(Continued)

(56) References Cited

U.S. PATENT DOCUMENTS

| 4,323,440 A | 4/1982 | Akatsuka |
| 4,338,174 A | 7/1982 | Tamura |

(Continued)

FOREIGN PATENT DOCUMENTS

| CN | 101523199 A | 9/2009 |
| JP | 08-511625 A | 12/1996 |

(Continued)

OTHER PUBLICATIONS

Gao, Fu "Determination of N2O in atmosphere by GC-ECD method and optimization of conditions thereof" China Petroleum and Chemical Standard and Quality, Sep. 30, 2012.

(Continued)

*Primary Examiner* — Walter L Lindsay, Jr.
*Assistant Examiner* — Philip Marcus T Fadul
(74) *Attorney, Agent, or Firm* — Knobbe Martens Olson & Bear LLP

(57) ABSTRACT

There is presented an electrochemical sensor (100) for sensing nitrous oxide ($N_2O$) in an associated volume (106), the sensor comprising a primary chamber (110), a secondary chamber (120) being placed adjacent the primary chamber (110), the secondary chamber (120) comprising electrodes for performing electrochemical measurements and furthermore an electrolyte comprising an aprotic solvent. A first membrane (114) and a secondary membrane (124) are permeable to nitrous oxide and may be arranged so as to separate the associated volume (106) from a primary volume (116) within the primary chamber (110), and the primary volume (116) from a secondary volume (126) within the secondary chamber (120), where the primary chamber (110)

(Continued)

comprises means for hindering oxygen in passing into the secondary volume (126), and wherein the working electrode (104) comprises indium (In).

19 Claims, 16 Drawing Sheets

(58) Field of Classification Search
USPC .................................................. 73/31.05
See application file for complete search history.

(56) References Cited

U.S. PATENT DOCUMENTS

| | | | |
|---|---|---|---|
| 4,651,292 A | | 3/1987 | Jeenicke et al. |
| 4,957,615 A | * | 9/1990 | Ushizawa ............ G01N 27/404 204/414 |
| 6,303,018 B1 | | 10/2001 | Holl et al. |
| 6,596,154 B1 | * | 7/2003 | Kjær ........................ C12Q 1/02 204/403.01 |
| 2002/0020210 A1 | | 2/2002 | Murase et al. |
| 2002/0182739 A1 | * | 12/2002 | Sadik ..................... G01N 30/02 436/106 |
| 2008/0092624 A1 | | 4/2008 | Scheffler |
| 2009/0054798 A1 | * | 2/2009 | Varney .................. A61B 5/083 600/532 |
| 2010/0288023 A1 | | 11/2010 | Leyer et al. |
| 2011/0309841 A1 | | 12/2011 | Oberndorfer et al. |
| 2012/0309982 A1 | * | 12/2012 | Shinohara ................ C07F 5/02 548/110 |

FOREIGN PATENT DOCUMENTS

| | | |
|---|---|---|
| JP | 2001-505662 A | 4/2001 |
| JP | 2009-187262 A | 8/2009 |
| WO | WO 97/19345 A1 | 5/1997 |
| WO | WO 98/21309 A1 | 5/1998 |
| WO | WO 99/15889 A1 | 4/1999 |
| WO | WO 99/45376 A1 | 9/1999 |
| WO | WO 01/57243 A1 | 8/2001 |
| WO | WO 2007/023283 A2 | 3/2007 |

OTHER PUBLICATIONS

First Office Action for Chinese Patent Application 201380068936.1, dated May 10, 2016.
Andersen, Knud et al., "An oxygen insensitive microsensor for nitrous oxide" Sensors and Actuators, 2001, pp. 42-48, vol. 81.
Revsbech, Niels Peter et al., "Combined Oxygen and Nitrous Oxide Microsensor for Denitrification Studies" Applied and Environmental Microbiology, Sep. 1988, pp. 2245-2249, vol. 54, No. 9.
Revsbech, Niels Peter et al., "Analysis of Microbial Communities with Electrochemical Microsensors and Microscale Biosensors" Methods in Enzymology, 2005, pp. 147-166, vol. 397.
Nexans—A self-protective sensor—http://www.nexans.com/eservice/Corporate-en/navigatepub_183976_-31783/A self protective sensor.html.
Rechner Sensors—Protection Caps and Protection Sets—http://www.industryarea.com/Capacitive-sensors-Y2093-S183-catalogue.html.
International Search Report for PCT/DK2013/050454 dated Apr. 3, 2014.

* cited by examiner

1635

ELECTROCHEMICAL SENSOR FOR SENSING NITROUS OXIDE

CROSS REFERENCE TO RELATED APPLICATIONS

This application is a U.S. National Phase Application of PCT International Application Number PCT/DK2013/050454, filed on Dec. 20, 2013, designating the United States of America and published in the English language, which is an International Application of and claims the benefit of priority to Danish Patent Application No. PA 2012 70834, filed on Dec. 28, 2012, and Danish Patent Application No. BA 2012 00200, filed on Dec. 28, 2012. The disclosures of the above-referenced applications are hereby expressly incorporated by reference in their entireties.

FIELD OF THE INVENTION

The present invention relates to electrochemical sensors and more particularly to electrochemical sensors for sensing nitrous oxide and corresponding methods and use.

BACKGROUND OF THE INVENTION

For numerous purposes, such as environmental monitoring, biological research, or wastewater treatment, it is beneficial to be able to sense or quantitatively measure nitrous oxide. Sensors for measuring nitrous oxide have previously been proposed, but may be seen as slow and/or bulky.

A sensor for measuring nitrous oxide has been proposed in the article "An oxygen insensitive microsensor for nitrous oxide", by Knud Andersen, Thomas Kjaer and Niels Peter Revsbech, Sensors and Actuators B 81 (2001) 42-48, which describes a method to create an $O_2$ insensitive and fast responding microsensor for $N_2O$. The elimination of $O_2$ interference was obtained by attaching a capillary with an alkaline solution of ascorbate in front of the tip of an electrochemical microsensor that was sensitive to both $O_2$ and $N_2O$. A 0.1 mm layer of 2 M ascorbate at pH 12 was able to remove all $O_2$ when measuring in air-saturated solutions ($O_2$ partial pressure 21 kPa), and no reduction of $N_2O$ by the ascorbate was observed. The response of the sensor to $N_2O$ was linear from 0 to 1.2 mM, and the detection limit was less than 1 μM. The tip diameters of the sensors described in detail were 50-80 micrometer, but much smaller sensors can be constructed. The 90% response times were about 40-50 s. Interference of carbon dioxide was shown to be negligible with respect to environmental monitoring, and the sensitivity to acetylene, which is commonly used to inhibit nitrous oxide reductase in denitrification studies, could be kept sufficiently low for experimental work.

An improved sensor for sensing nitrous oxide would be advantageous, and in particular a more efficient, sensitive, durable, compact and/or reliable sensor would be advantageous.

SUMMARY OF THE INVENTION

It may be seen as advantageous to provide a more efficient, sensitive, durable, compact, stable, temperature insensitive and/or reliable sensor for sensing nitrous oxide. It may also be seen as a further object of the present invention to provide an alternative to the prior art. To better address one or more of these concerns, in a first aspect of the invention there is provided an electrochemical sensor (100) for sensing nitrous oxide ($N_2O$) in an associated volume (106), the sensor comprising a primary chamber (110) having a primary opening (112) towards the associated volume (106), a secondary chamber (120) being placed adjacent the primary chamber (110) or partially surrounded by the primary chamber (110), the secondary chamber (120) comprising, A working electrode (104), A reference electrode (108), and An electrolyte comprising an aprotic solvent, where the secondary chamber (120) has a secondary opening (122) towards the primary chamber (110), where a secondary membrane (124) is placed in the secondary opening (122), wherein the secondary membrane (124) is permeable to nitrous oxide and is arranged so as to separate a primary volume (116) from a secondary volume (126), said secondary volume being within the secondary chamber (120), said primary volume being within the primary chamber (110), where the primary chamber (110) comprises means for hindering oxygen in passing into the secondary volume (126), and wherein the working electrode (104) comprises indium (In).

The wording of "secondary (membrane)" enables distinguishing the secondary membrane from other membranes, such as a primary membrane, such as enables distinguishing "secondary membrane" from "primary membrane". It is understood that "secondary membrane" does not imply the presence of a "primary membrane". Throughout this application, "secondary membrane" is and/or may be used interchangeably with "secondary opening membrane". Throughout this application, "primary membrane" is and/or may be used interchangeably with "primary opening membrane" and "first membrane".

In another embodiment, there is provided an electrochemical sensor (100) for sensing nitrous oxide ($N_2O$) in an associated volume (106), the sensor comprising a primary chamber (110) having a primary opening (112) towards the associated volume (106), where a primary membrane (114) is placed in the primary opening, a secondary chamber (120) being placed adjacent the primary chamber (110) or partially surrounded by the primary chamber (110), such as within the primary chamber (110), the secondary chamber (120) comprising, A working electrode (104), A reference electrode (108), optionally a guard electrode (109), and An electrolyte comprising an aprotic solvent, such as electrolyte comprising an aprotic solvent wherein an ionic compound is dissolved, where the electrolyte electrically connects the reference electrode and the working electrode and the optional guard electrode (109), where the secondary chamber (120) has a secondary opening (122) towards the primary chamber (110), where a secondary membrane (124) is placed the secondary opening (122), wherein the primary membrane (114) is permeable to nitrous oxide and is arranged so as to separate the associated volume (106) from a primary volume (116), said primary volume being within the primary chamber (110), and where the secondary membrane (124) is permeable to nitrous oxide and is arranged so as to separate the primary volume (116) from the a secondary volume (126), said secondary volume being within the secondary chamber, where the primary chamber (110) comprises a means for hindering oxygen in passing into the secondary volume (126), such as hindering oxygen in passing from the associated volume (106) through the primary volume (116) and into the secondary volume (126), and wherein the working electrode (104) comprises indium (In).

The invention is particularly, but not exclusively, advantageous for obtaining an improved sensor for sensing nitrous oxide, and in particular a more efficient, sensitive, durable, compact and/or reliable sensor. It may in particular be seen as advantageous to utilize the catalytic capabilities of the metal indium to facilitate the reduction of nitrous oxide at the surface of the working electrode, such as to enable use of a relatively low polarization voltage, which in turn realizes a relatively low zero-current. It may thus be noted, that it may be seen as the gist of the invention, to utilize the basic insight made by the inventors, that use of indium in the working electrode enables obtaining a relatively high sensor response for a given concentration of nitrous oxide, and at the same time a relatively low, stable and temperature insensitive zero-current which altogether enables a high signal-to-noise ratio. The polarization level is understood to be the voltage applied between the working electrode and the reference electrode.

Furthermore, it should be recognized, that the present inventors have realized through inventiveness and massive research that despite having the electrolyte being based on an aprotic solvent, in the particular sensor described in the independent claim, water vapour may nevertheless find its way to the working electrode and cause a zero-current, such as an elevated zero-current, due to proton reduction. While other materials of the working electrode may yield a higher response, this basic insight prompted the selection of a new and inventive material for use in the working electrode, which not only exhibited catalytic properties for $N_2O$ reduction, but which also realized a tolerable zero-current, and which in consequence enabled a better ratio between zero-current and response.

By 'electrochemical sensor' is understood a sensor that detects the presence, such as measure the concentration, of an analyte, such as nitrous oxide ($N_2O$), by oxidizing or reducing the analyte at an electrode and detecting, such as measuring, the resulting current. It is understood that the resulting current need not necessarily be measured as a current, but may for example be measured as a voltage drop across a resistor. The word 'sensor', 'electrochemical sensor', and 'electrochemical sensor for sensing nitrous oxide (N2O)' are generally used interchangeably within the context of the present application. An example of an electrochemical sensor is described in the article "An oxygen insensitive microsensor for nitrous oxide", by Knud Andersen, Thomas Kjaer and Niels Peter Revsbech, Sensors and Actuators B 81 (2001) 42-48, which is hereby incorporated by reference in entirety, and a particular reference is made to section 2.1 describing sensor construction.

By 'analyte' is understood the compound of interest, such as a molecule, such as nitrous oxide.

By 'sensing' is understood qualitatively detecting the presence of an analyte. In some more specific embodiments, sensing may be construed as quantitatively measuring a concentration of an analyte.

By 'nitrous oxide ($N_2O$)' is understood a chemical compound being a molecule with the formula $N_2O$ (N2O). Nitrous oxide may also be referred to as dinitric oxide or laughing gas.

By 'associated volume' is understood an associated volume which is adjacent the sensor and which may contain nitrous oxide. The associated volume is not to be construed as limiting to the scope of the claims. The concentration of nitrous oxide in the associated volume may be measured with the sensor. The associated volume may comprise a fluid, a gas or a matrix, such as a biofilm, such as an extracellular matrix.

By 'primary chamber' is understood a chamber, such as a casing, which delimits a primary volume within the primary chamber from the surroundings external to the primary chamber. However, it is encompassed by the present invention, that the primary chamber may have one or more through-going holes in the delimiting walls, such as openings for electrical wiring or membranes. However, in general, the primary chamber does not allow fluid passage from outside the primary chamber to inside the primary chamber. In particular embodiments, the primary chamber may comprise walls made at least partially of glass. In particular embodiments, the primary chamber may comprise walls made at least partially of a polymeric material, such as polyether ether ketone (PEEK).

By 'primary opening' is understood a through-going hole in the walls of the primary chamber which through-going opening connects the associated volume with a primary volume within the primary chamber.

By 'primary membrane' is understood a membrane material which is placed in the primary opening. The primary membrane is arranged so as to separate the associated volume from the primary volume within the primary chamber. More specifically, the primary membrane is situated so as to fill the primary opening, so as to block passage from the associated volume to the primary volume of any substance incapable of penetrating through the primary membrane. It is understood, that the primary membrane may refer to a thin, film-like structure that separates two fluids, such as a liquid or gas in the associated volume, and a liquid or gas in the primary volume. However, it is also understood that the primary membrane may act as a selective barrier, allowing some particles or chemicals to pass through but not others. It is in particular understood, that the primary membrane is permeable to nitrous oxide. The primary membrane may in particular embodiment comprise, such as consist of, silicone, such as any one of the silicone sealants obtainable from Dow Corning with product number 732 or 734. A possible advantage of using silicone as primary membrane material may be that it combines good adhesion to glass with high permeability to $N_2O$.

It may be understood, that in certain embodiments, the primary membrane may be dispensed with. It may be understood, that in some of these embodiments, there is provided means for keeping unwanted substances out of the primary volume, such as avoiding unwanted substances in reaching the secondary membrane. In an exemplary embodiment, the primary chamber is divided into sub-chambers, which performs various functions, such as one sub-chamber being a meander shaped pathway with reactive walls, such as membranes through which scavengers, such as oxygen scavengers, may diffuse, or through which the unwanted substances may diffuse. In such embodiment, an unwanted substance may enter partially into the primary chamber, such as a primary sub-chamber, but may not reach the secondary membrane, or may reach the secondary membrane only in minute concentrations.

By 'secondary chamber' is understood a chamber, such as a casing, which delimits a secondary volume within the secondary chamber from the surroundings external to the secondary chamber. The secondary chamber is understood to be placed adjacent the primary chamber or partially surrounded by the primary chamber, such as within the primary chamber. However, it is encompassed by the present invention, that the secondary chamber may have one or more through-going holes in the delimiting walls, such as openings for electrical wiring or membranes. However, in general, the secondary chamber does not allow fluid passage from outside the secondary chamber to inside the secondary chamber. In particular embodiments, the secondary chamber may comprise walls made at least partially of glass. In particular embodiments, the secondary chamber may comprise walls made at least partially of a polymeric material, such as polyether ether ketone (PEEK).

It is understood, that 'adjacent' in this context is not to be construed as limiting to embodiments where the entire primary chamber is in close contact, such as borders, the secondary chamber. In certain embodiments, the primary chamber may comprise portions being distant from the secondary chamber. It may furthermore be understood, that the primary chamber may be split into several primary sub-chambers, such as a primary sub-chamber being arranged for comprising a primary substance and another primary sub-chamber for ensuring passage of, e.g., a gas from the associated volume to the secondary membrane. In such arrangement, the sample may come into contact with the oxygen scavenger through an internal membrane in the primary chamber, which internal membrane separates the primary sub-chambers.

By 'secondary opening' is understood a through-going hole in the walls of the secondary chamber which through-going opening connects the primary volume with a secondary volume within the secondary chamber.

By 'secondary membrane' is understood a membrane material which is placed in the secondary opening. The secondary membrane is arranged so as to separate the primary volume from the secondary volume within the secondary chamber. More specifically, the secondary membrane is situated so as to fill the secondary opening, so as to block passage from the primary volume to the secondary volume of any substance incapable of penetrating through the secondary membrane. It is understood, that the secondary membrane may refer to a thin, film-like structure that separates two fluids, such as a liquid or gas in the primary volume, and a liquid or gas in the secondary volume. However, it is also understood that the secondary membrane may act as a selective barrier, allowing some particles or chemicals to pass through but not others. It is in particular understood, that the secondary membrane is permeable to nitrous oxide. The secondary membrane may in particular embodiment comprise, such as consist of, silicone, such as any one of the silicone sealants obtainable from Dow Corning with product number 732 or 734. A possible advantage of using silicone as secondary membrane material may be that it combines good adhesion to glass with high permeability to $N_2O$.

'Working electrode' is known in the art, and understood to be the electrode the electrochemical sensor on which the reaction of interest is occurring. It may be understood that the reduction of nitrous oxide is taking place at the working electrode. It may be understood that the working electrode may be understood as the cathodic electrode or the cathode.

'Reference electrode' is known in the art, and understood to be the electrode the electrochemical sensor on which acts as reference in measuring and controlling the working electrodes potential. It may be understood that the reference electrode may be referred to in the present applications as the anodic electrode or the anode. In particular embodiments there may be used silver (Ag) in or on the reference electrode.

By 'guard electrode' is understood an additional electrode, such as an additional cathode, which is arranged so as to remove oxygen diffusing toward the working electrode from the secondary chamber. In particular embodiments, the working electrode is placed somewhat towards one end of the primary chamber, such as the end with the secondary opening, such as near the secondary opening, and the guard electrode is placed between the working electrode and a middle portion of the primary chamber. A guard electrode is described in "An oxygen microsensor with a guard cathode", NP Revsbech, Limnol. Oceanogr., 34(2), 1989, 474-478, which is hereby incorporated by reference in entirety.

By 'electrolyte' is understood a liquid comprising ions. The electrolyte is understood to be electrically conducting. It is understood that the electrolyte electrically connects the reference electrode and the working electrode. The charge carriers are dissolved ionic compounds.

'Aprotic solvent' is known in the art and understood to be a solvent which cannot donate protons. Examples include propylene carbonate, dimethyl sulfoxide (DMSO), acetonitrile (MeCN), dimethylformamide (DMF), acetone, ethyl acetate (EtOAc), tetrahydrofuran (THF). The present inventors have made the insight that an advantage of employing an aprotic solvent in the sensor may be that the zero-current is lowered, since less protons is available for reduction into $H_2$ molecules.

By 'ionic compound' is understood compounds held together by ionic forces. Ionic compounds may, however, be dissolved in some fluids, such as TBA-I being dissolved in propylene carbonate so as to form TBA ions and iodide ions.

By 'means for hindering oxygen in passing' is understood means which hinders oxygen in passing from the associated volume, such as the outside of the sensor, through the primary membrane, the primary volume and the secondary membrane. It may thus be understood, that the means for hindering oxygen in passing enables keeping oxygen from the associated volume substantially out of the secondary volume. The means for hindering oxygen in passing may function by, for example blocking or degrading oxygen before it reaches the secondary volume. The means for hindering oxygen in passing may comprise a primary substance, such as a chemically active entity which degrades oxygen, such as an oxygen scavenger. In another embodiment, the means for hindering oxygen in passing may be a selective barrier being impermeable to oxygen.

In a specific embodiment, the 'means for hindering oxygen in passing into the secondary volume' comprises 'means for hindering a diffusion of oxygen' by which is understood means which hinders diffusion of oxygen, such as freely diffusing oxygen, from the associated volume, such as the outside of the sensor, through the primary membrane, the primary volume and the secondary membrane. The means for hindering a diffusion of oxygen may comprise a primary substance, such as a chemically active entity which degrades oxygen, such as an oxygen scavenger. In another embodiment, the means for hindering a diffusion of oxygen may be a selective barrier being impermeable to oxygen.

However, the means for hindering oxygen in passing into the secondary volume is not limited exclusively to blocking diffusion of oxygen, but may also in certain embodiments be arranged so as to block passage of oxygen in a sample which is actively led through the primary chamber.

In a particular embodiment there is provided an electrochemical sensor, wherein a sample may be actively moved through or over an oxygen scavenger in the primary chamber, and wherein there is further provided means for hindering a passage of oxygen (in the actively led sample) towards the secondary membrane. In a specific exemplary embodiment, the primary chamber is arranged for enabling a gas sample to be actively pumped through a solution comprising ascorbate before it reaches the secondary membrane, wherein the ascorbate hinders a passage of oxygen towards the secondary membrane. In another specific embodiment, the primary chamber is arranged for enabling a sample to be actively pumped through a passageway in the primary chamber, which passageway is bordered by an internal membrane within the primary chamber, behind which internal membrane an oxygen scavenger is present, which oxygen scavenger enables removing oxygen from the actively led sample before it reaches the secondary membrane.

It may in general be understood to be advantageous to hinder oxygen in passing into the secondary chamber, since if the oxygen passes into the secondary chamber, it may interfere with the measurement of nitrous oxide, since oxygen may pass electrons to the working electrode under the same conditions as nitrous oxide passes electrons to the working electrode. In other words, both nitrous oxide and oxygen may cause a current to flow through the working electrode, and in case the current is caused by oxygen it may thus interfere with the measurement of nitrous oxide.

By 'primary substance' is understood any substance which is capable of hindering passage of oxygen from the associated volume through the primary volume and into the secondary volume. The primary substance may block passage of oxygen or it may consume oxygen, such as consume the oxygen chemically as described in the scientific article "An oxygen insensitive microsensor for nitrous oxide", by Knud Andersen, Thomas Kjaer and Niels Peter Revsbech, Sensors and Actuators B 81 (2001) 42-48, which is hereby incorporated by reference. For examples of primary substances, reference is made to the patent application WO 99/15889 which is hereby incorporated by reference.

By 'the working electrode comprises indium (In)' is understood that the working electrode is arranged such that the catalytic properties of the element Indium (no. 49 in the periodic table) towards reduction of nitrous oxide are utilized. In an exemplary embodiment, indium is used as working electrode. In another embodiment, indium is deposited on the working electrode. Indium may be understood to be elemental indium. In another embodiment, indium may be understood to be, or comprise, indium, such as indium ions, such as indium oxide ($In_2O_3$).

In another embodiment there is provided an electrochemical sensor, wherein the aprotic solvent is propylene carbonate,
wherein the means for hindering oxygen in passing comprises ascorbate, and
wherein an ionic compound is dissolved in the electrolyte, the ionic compound being chosen from the group comprising:
tetrabutylammonium iodide (TBA-I),
tetrabutylammonium chlorate (TBA-Cl),
tetrabutylammonium flouroborate (TBA-$BF_4$) and/or
tetrabutylammonium perchlorate (TBA-$ClO_4$).

This embodiment may be seen as an exemplary, advantageous embodiment for yielding a sensor with an improved performance in terms of signal to noise ratio.

In another embodiment there is provided an electrochemical sensor, wherein a secondary opening membrane length (L), said secondary opening membrane length being a length of the secondary opening membrane in a direction from the primary chamber to the secondary chamber through the secondary opening membrane, is longer than 25 micrometer, such as 30 micrometer or longer, such as 35 micrometer or longer, such as 40 micrometer or longer, such as 45 micrometer or longer, such as 50 micrometer or longer, such as 60 micrometer or longer, such as 70 micrometer or longer, such as 80 micrometer or longer, such as 90 micrometer or longer, such as 100 micrometer or longer, such as 110 micrometer or longer, such as 120 micrometer or longer, such as 130 micrometer or longer, such as 140 micrometer or longer, such as 150 micrometer or longer.

An advantage of having a relatively long membrane may be that it enables providing an electrochemical sensor which produces less noise, i.e., a lower base line, which in turn consequently enables producing better signal-to-noise ratios.

Another advantage of having a relatively long membrane may be that it enables providing an electrochemical sensor which is more reliable, such as has a longer life expectancy. An advantage may be that for sets of (a plurality of) electrochemical sensors with longer membranes, all sensors (i.e., 100%) work for longer time before break down (such as sudden increase in noise) of the first sensor in the set.

By 'secondary opening membrane length" may be understood a length, such as a minimum length, which an entity (such as a molecule (such as $H_2O$), such as an analyte (such as $N_2O$) and/or an interfering species (such as $O_2$)) originally placed in the primary chamber would need to travel through the secondary opening membrane in order to get into the secondary chamber through the secondary opening membrane. It may be understood that the primary chamber, the secondary chamber, the secondary opening and/or the secondary opening membrane are arranged so that said entity can realistically only, such as only, pass from the primary chamber to the secondary chamber through the membrane, such as by passing through at least a length corresponding to the secondary opening membrane length through the secondary opening membrane. The secondary opening membrane length may be understood to be measured under standard conditions for temperature and pressure, such as at a temperature of 273.15 K (0° C., 32° F.) and an absolute pressure of 100 kPa (14.504 psi, 0.987 atm, 1 bar).

In another embodiment there is provided an electrochemical sensor, wherein a secondary opening membrane length (L), said secondary opening membrane length being a length of the secondary opening membrane in a direction from the primary chamber to the secondary chamber through the secondary opening membrane, is 50 micrometer or longer.

In another embodiment there is provided an electrochemical sensor, wherein a secondary opening membrane length (L), said secondary opening membrane length being a length of the secondary opening membrane in a direction from the primary chamber to the secondary chamber through the secondary opening membrane, is 100 micrometer or longer.

In another embodiment there is provided an electrochemical sensor, wherein a secondary opening membrane length (L), said secondary opening membrane length being a length of the secondary opening membrane in a direction from the primary chamber to the secondary chamber through the secondary opening membrane, is 5 millimeter or shorter. In alternative embodiments, the secondary opening membrane length is 10 centimeter or shorter, such as 5 centimeter or shorter, such as 1 centimeter or shorter, such as 2 millimeter or shorter, such as 1 millimeter or shorter, such as 0.5 millimeter or shorter, such as 250 micrometer or shorter, such as 200 micrometer or shorter.

An advantage of having a relatively short membrane may be that it enables entities, such as an analyte, to travel faster through the membrane, which in turn enables a shorter response time, i.e., a faster responding sensor. An advantage of having a short membrane may be that it enables reaching a better sensitivity.

In alternative embodiments, the secondary opening membrane length is within 25 micrometer and 5 millimeter, such as within 25 micrometer and 1 millimeter, such as within 25 micrometer and 200 micrometer, such as within 25 micrometer and 150 micrometer. In alternative embodiments, the secondary opening membrane length is within 50 micrometer and 5 millimeter, such as within 50 micrometer and 1 millimeter, such as within 50 micrometer and 200 micrometer, such as within 50 micrometer and 150 micrometer. In alternative embodiments, the secondary opening membrane length is within 100 micrometer and 5 millimeter, such as within 100 micrometer and 1 millimeter, such as within 100 micrometer and 200 micrometer, such as within 100 micrometer and 150 micrometer. In all of the intervals in this paragraph, both end points are excluded.

In another embodiment there is provided an electrochemical sensor, wherein a detection limit in liquid is less than 1000 nM, such as less than 750 nM, such as less than 500 nM, such as less than 350 nM, such as less than 100 nM, such as 90 nM or less, such as 80 nM or less, such as 70 nM or less. In another embodiment there is provided an electrochemical sensor, wherein a detection limit in gas is 100 ppm or less, such as 75 ppm or less, such as 50 ppm or less, such as 25 ppm or less, such as 10 ppm or less, such as 5 ppm or less, such as 1 ppm or less, such as 0.9 ppm or less, such as 0.8 ppm or less, such as 0.7 ppm or less, such as 0.6 ppm or less. In both cases, the detection limit may be determined by twice the noise amplitude divided with the analytical sensitivity. The noise and analytical sensitivity may be determined at room temperature and without employing electric shielding. An advantage of having a low detection limit may be that the electrochemical sensor is able to detect a smaller amount of nitrous oxide. It may also be understood, that the detection limit is equivalent with the resolution, i.e., the low detection limit enables resolving, such as quantifying, a concentration of nitrous oxide more precisely. Another possible advantage may be that a low detection limit, such as a low resolution enables detecting smaller changes in the concentration of nitrous oxide.

In another embodiment there is provided an electrochemical sensor, wherein a baseline signal can be kept below 50 pA, such as below 40 pA, such as below 30 pA, such as below 20 pA, such as below 10 pA, such as below 5 pA. A possible advantage of having a low baseline signal may be that relatively small signals from the reduction of nitrous oxide may then be detected and/or quantified. Baseline signal may be used interchangeably with 'zero-current'. It is understood, that the level of the baseline signal may influence the noise level. The baseline signal may for example be susceptible to external influences, such as temperature, which may thus cause noise. An advantage of having lower baseline signal may then be that less noise is generated. It is generally understood that less noise enables detection of lower levels of nitrous oxide. Another possible advantage of having a small baseline signal may be that it enables a better resolution in terms of quantifying a concentration of nitrous oxide, such as enabling a lower detection limit. Another possible advantage of having a small baseline signal, such as a low zero-current, may be that it enables good temperature stability, i.e., the effect of temperature on the baseline signal is relatively low.

In another embodiment there is provided an electrochemical sensor, wherein a sensor response is at least 100 pA/100 micromolar $N_2O$, such as at least 150 pA/100 micromolar $N_2O$, such as at least 200 pA/100 micromolar $N_2O$, such as at least 250 pA/100 micromolar $N_2O$, such as at least 300 pA/100 micromolar $N_2O$. Sensor response is understood to be the signal arising from reduction of nitrous oxide. Sensor response may be referred to as 'signal'. It is understood that an advantage of having a large response may be that it enables detecting smaller levels of nitrous oxide. Another possible advantage of having a large response may be that it enables a better resolution in terms of quantifying a concentration of nitrous oxide.

In another embodiment there is provided an electrochemical sensor, wherein a ratio between a sensor response and a baseline signal is at least 10 (pA/100 micromolar $N_2O$)/(pA), such as at least 20 (pA/100 micromolar $N_2O$)/(pA), such as at least 30 (pA/100 micromolar $N_2O$)/(pA), such as at least 40 (pA/100 micromolar $N_2O$)/(pA), such as at least 50 (pA/100 micromolar $N_2O$)/(pA), such as at least 60 (pA/100 micromolar $N_2O$)/(pA), such as at least 70 (pA/100 micromolar $N_2O$)/(pA). The ratio between a sensor response and a baseline signal may be understood to influence the signal-to-noise ratio, where higher sensor response with respect to baseline signal may be understood to facilitate higher signal-to-noise ratio. It is understood that an advantage of having a large signal-to-noise ratio may be that it enables detecting smaller levels of nitrous oxide. Another possible advantage of having a large signal-to-noise ratio may be that it enables a better resolution in terms of quantifying a concentration of nitrous oxide.

In another embodiment there is provided an electrochemical sensor, the sensor response and/or the baseline signal is substantially stable over extended periods of time, such as substantially stable over 30 days, such as 60 days, such as 90 days. By substantially stable may be understood that the baseline signal may be within ±100% of an initial value, such as within ±50% of an initial value. By substantially stable may be understood that the response signal may be within ±100% of an initial value, such as within ±50% of an initial value, such as within ±25% of an initial value, such as within ±10% of an initial value.

In another embodiment there is provided an electrochemical sensor, wherein the aprotic solvent is propylene carbonate. An advantage of propylene carbonate (PC) may be that it enables dissolving ionic compounds, such as compounds comprising tetrabutylammonium, such as TBA-I, TBA-Cl, TBA-$BF_4$ or TBA-$ClO_4$. Another possible advantage may be that PC does not degrade commonly used membrane materials, such as silicone. Another possible advantage is that it is non-toxic.

In another embodiment there is provided an electrochemical sensor, wherein the 'means for hindering oxygen in passing into the secondary volume' comprises an oxygen scavenger. An 'oxygen scavenger' is understood to be a chemical substance added which may be able to hinder a passing of oxygen, such as diffusion of oxygen, by removing or absorbing oxygen. In an exemplary embodiment an antioxidant may be used, such as ascorbate, a gallate or a sulphide, but in principle a broad range of all current antioxidants are applicable.

In specific embodiments, where the primary chamber comprises a freely diffusing oxygen scavenger, the primary chamber may be arranged so that a diffusion of the oxygen scavenger into a volume in front of the second membrane (from the remaining portion of the primary volume) may at least be large enough to balance the consumption of the oxygen scavenger in the region in front of the second membrane. In specific embodiments, the volume in front of the second membrane may correspond to a volume between the primary membrane and the secondary membrane, and the remaining portion of the primary volume, which may be referred to as a "bulk" volume, may be large enough in order to effectively act as a reservoir for the oxygen scavenger.

In a particular embodiment, the oxygen scavenger is ascorbate, and un-oxidized ascorbate is supplied from the bulk reservoir to the volume in front of the second membrane by diffusion. Products from the reaction between oxygen and ascorbate are removed to the bulk volume also by diffusion. In a specific embodiment, the diameter of the secondary membrane should be as large as possible (to capture all incoming $N_2O$) without compromising a necessary rate of diffusion of fresh ascorbate to the volume in front of the secondary membrane.

In another embodiment there is provided an electrochemical sensor, wherein the means for hindering oxygen in passing into the secondary volume comprises ascorbate. For a specific example of application of ascorbate, reference is made to the article "An oxygen insensitive microsensor for nitrous oxide", by Knud Andersen, Thomas Kjaer and Niels Peter Revsbech, Sensors and Actuators B 81 (2001) 42-48, which is hereby incorporated by reference, and in particular reference is made to section 3.1, entitled "Oxygen penetration into the guard".

In another embodiment there is provided an electrochemical sensor, wherein the primary chamber has a volume of at least 0.5 mL. A possible advantage of having a primary chamber of at least this volume may be, that it enables holding larger quantities of, e.g., the primary substance, which in turn means that it takes longer time to consume the primary substance. This is in particular relevant in cases where the primary substance is consumed in a process where oxygen is degraded. This may for example be the case where the primary substance is given by ascorbate. In consequence, a larger primary chamber may ensure that the lifetime of the primary substance is extended (since the consumption of more of the primary substance, such as ascorbate, takes longer time). In other embodiments, the primary chamber has a volume of at least 0.1 mL, such as at least 0.25 mL, such as at least 0.5 mL, such as at least 0.75 mL, such as at least 1 mL, such as at least 2, 3, 4, 5, 6, 7, 8, 9, or 10 mL. In a particular embodiment, the primary chamber has a volume of at least 5 mL.

In another embodiment there is provided an electrochemical sensor, wherein an ionic compound is dissolved in the electrolyte, the ionic compound comprising tetrabutylammonium (TBA). An advantage of using TBA may be, that it has proven to be able to provide promising results in terms of sensor performance. In another embodiment there is provided an electrochemical sensor, wherein an ionic compound is dissolved in the electrolyte, the ionic compound being chosen from the group comprising
  tetrabutylammonium iodide (TBA-I),
  tetrabutylammonium chlorate (TBA-Cl),
  tetrabutylammonium flouroborate (TBA-$BF_4$) and/or tetrabutylammonium perchlorate (TBA-$ClO_4$).

In another embodiment there is provided an electrochemical sensor, wherein the sensor is suited for measuring in any one of: a gas, a liquid. By a gas may be understood a substantially pure gas, such as a pure gas, or there may be understood a gas mixture, such as air.

In another embodiment there is provided an electrochemical sensor, wherein the sensor further comprises a rigid cover serving to protect the sensor. This may in particular be advantageous for measurements where the conditions generally are rough, such as for use in industrial facilities, such as for use in a wastewater treatment facility. In a particular embodiment, the rigid cover is a cover of a material being less brittle than glass, such as metal, such as steel, such as stainless steel, such as aluminium. In a particular embodiment, the rigid cover is arranged so that the first chamber and the second chamber cannot come into physical contact with planar surfaces. An advantage of this may be, that the first and second chamber, which may be relatively fragile compared to the rigid cover, is less likely to be damaged by planar surfaces such as floors and walls of containers. In an embodiment, the rigid cover has a length along the longitudinal axis of the sensor which is at least as long as the distance between the most distant point on the first chamber and the second chamber. In an embodiment, the rigid cover is made of an electrically conducting material and serves as a faraday cage, such as enabling shielding of external electric fields. An advantage of this may be that it enables reducing noise caused by external electric fields. In a particular embodiment, the rigid cover is formed so as to avoid that gas bubbles may be trapped adjacent to the first or second chamber, such as by having holes in the rigid cover which allows bubbles to escape from a region adjacent to the first or second chamber. An advantage of such rigid cover may be that the first chamber and/or the second chamber can be relatively fragile while still having a relatively robust sensor due to the rigid cover. An advantage of this may be that a robust sensor with first chamber and/or second chamber made of thin materials, such as thin glass walls. This may in turn be advantageous since, e.g., thin glass walls are beneficial for production, e.g., for allowing optically inspecting the interior of the sensor during manufacture and/or quality control. Another possible advantage of having, e.g., thin glass walls may be, that they facilitate very small dimensions, which in turn enable very low response times.

The prior art sensors may not be applicable in routine measurements, such as standard online environmental measurements or online wastewater treatment, since the prior art sensor may be delicate with glass tips of about 30-50 µm. However, by employing a rigid cover as described above, optionally with an inner tubing, a more robust sensor may be provided.

In another embodiment there is provided an electrochemical sensor, wherein the sensor comprises means for enabling temperature compensation. The present inventors have made the insight that temperature may affect the noise and response of the sensor, and have exerted an inventive step by proposing means for enabling temperature compensation, such as the means for enabling temperature compensation being integrated in the electrochemical sensor. In another embodiment there is provided an electrochemical sensor, wherein the sensor comprises means for enabling temperature compensation, wherein the means for enabling temperature compensation comprises electronically stored information which enables compensating for the effects of temperature, such as the stored information being descriptive of the influence of temperature on the output of the sensor. In a specific embodiment, the effect of temperature may be parameterized, such as described with an equation of a general form, and the stored information corresponds to one or more numerical constants, such as 1, 2, 3, 4, 5, 6, 7, 8, 10 numerical constants, in the equation. An advantage of this may be, that anyone using the sensor may be informed by the relation between the temperature and the noise and response of the sensor, and make take these relations into account. Another advantage may be that this reduces, such as eliminates, the requirements in terms keeping temperature constants. This may in particular be advantageous for measurements where the temperature cannot be kept constant, such as for use in industrial facilities, such as for use in a wastewater treatment facility. In a specific embodiment, the sensor further comprises means for measuring temperature, such as a thermometer, which readily enables a user to take the temperature, or changes of temperature into account. In a specific embodiment, the temperature dependence is given by equations (7) and (10b) in the article "Temperature Dependence and Interferences of NO and $N_2O$ Microelectrodes Used in Wastewater Treatment", by Jenni et al., Environ. Sci. Technol. 2012, 46, 2257-2266, which is hereby incorporated by reference in entirety, where the constants a1, b1, a2 and b2 in equation (10b) may be determined, such as fitted, by 4 experiments (2 different temperatures, 2 different concentrations). However, it is also conceived that other mathematical formulas may represent temperature dependence and be employed for the purpose of compensating for, e.g., non-constant, temperatures.

In another embodiment there is provided an electrochemical sensor further comprising
- a voltage generating means, such as a potentiostat, for holding the working electrode at a first voltage with respect to the reference electrode, such that nitrous oxide may be reduced at the working electrode causing a current to flow through the electrode,
- a current sensing means, such as an ammeter, for sensing the presence of the current, such as quantifying the current.

In another embodiment there is provided an electrochemical sensor, wherein the sensor is arranged for providing real-time measurements, such as by providing a sensor of sufficiently small dimensions, such as enabling response time of less than 1 hr, such as less than 30 minutes, such as less than 15 minutes, such as less than 10 minutes, such as less than 5 minutes, such as less than 2 minutes, such as less than 90 seconds, 60 seconds, such as within 10-60 seconds. The response time is understood to be the period of time it takes before the response reaches 90% of the new equilibrium signal. In another embodiment there is provided an electrochemical sensor, wherein the sensor further comprises a third electrode working as a counter electrode. 'Counter electrode' is known in the art and understood as an electrode which can deliver or receive electrons (i.e., current) from the working electrode. The counter electrode may also be referred to as an auxiliary electrode. An advantage of such three-electrode setup may be that less current needs to be drawn from or to the reference electrode.

In a particular embodiment, there is provided a sensor which comprises a rigid cover as described above and temperature compensation means as described above. As opposed to the prior art sensors this particular sensor is applicable in routine measurements, such as standard online environmental measurements or online wastewater treatment, since the rigid cover provides robustness, even if the primary chamber comprises a delicate glass tip with diameter about 30-50 μm. The sensor according to the present embodiment may furthermore be seen as stable, such as long-term stable, and has optimized measurement properties in terms of low zero-current, low noise, and high response to nitrous oxide. An improved sensor for sensing nitrous oxide is thus provided, which is more robust, and which is capable of yielding more certain measurements. This may be of particular benefit during online routine measurements. Furthermore, a sensor enabling better, more precise and more reliable measurements (such as better signal-noise ratio, lower detection limit) is provided. Still further, a sensor is provided which is may be seen as substantially independent of the surrounding temperature due to the temperature compensation and/or decreased temperature sensitivity.

In a second aspect, the invention further relates to a method according to the independent method claim.

In a third aspect, the invention further relates to use of a sensor according to the first aspect for sensing the presence of, such as measuring quantitatively, nitrous oxide in an associated volume, such as the associated volume being occupied by wastewater, sea water, drinking water, gas emission from soil as earth surface or surface of a field. This aspect of the invention is particularly, but not exclusively, advantageous in that the sensor may advantageously be used for a large number of applications, such as environmental monitoring, such as biological research, such as sensing nitrous oxide in wastewater.

In a fourth aspect, the invention relates to a method of manufacture of a sensor according to the first aspect. In a particular embodiment, there is provided a method of manufacture of a sensor wherein the sensor comprises means for enabling temperature compensation, such as the means for enabling temperature compensation comprises electronically stored information which enables compensating for the effects of temperature, such as the stored information being descriptive of the influence of temperature on the output of the sensor, which method comprises the step of measuring the the effects of temperature, such as the influence of temperature on the output of the sensor, and providing corresponding means for enabling temperature compensation, such as electronically stored information comprising data enabling temperature compensation.

The first, second and third aspect of the present invention may each be combined with any of the other aspects. These and other aspects of the invention will be apparent from and elucidated with reference to the embodiments described hereinafter.

BRIEF DESCRIPTION OF THE FIGURES

The first, second and third aspect according to the invention will now be described in more detail with regard to the accompanying figures. The figures show one way of implementing the present invention and is not to be construed as being limiting to other possible embodiments falling within the scope of the attached claim set.

FIG. 5 is plot of the baseline signal (pA) as a function of the polarization voltage (V) for an electrochemical sensor when the working electrode comprises In.

FIG. 6 is plot of the signal in response to the exposure of $N_2O$ (PA/100 μM $N_2O$) as a function of the polarization voltage (V) for an electrochemical sensor when the working electrode comprises In.

DETAILED DESCRIPTION OF AN EMBODIMENT

Figure 1:
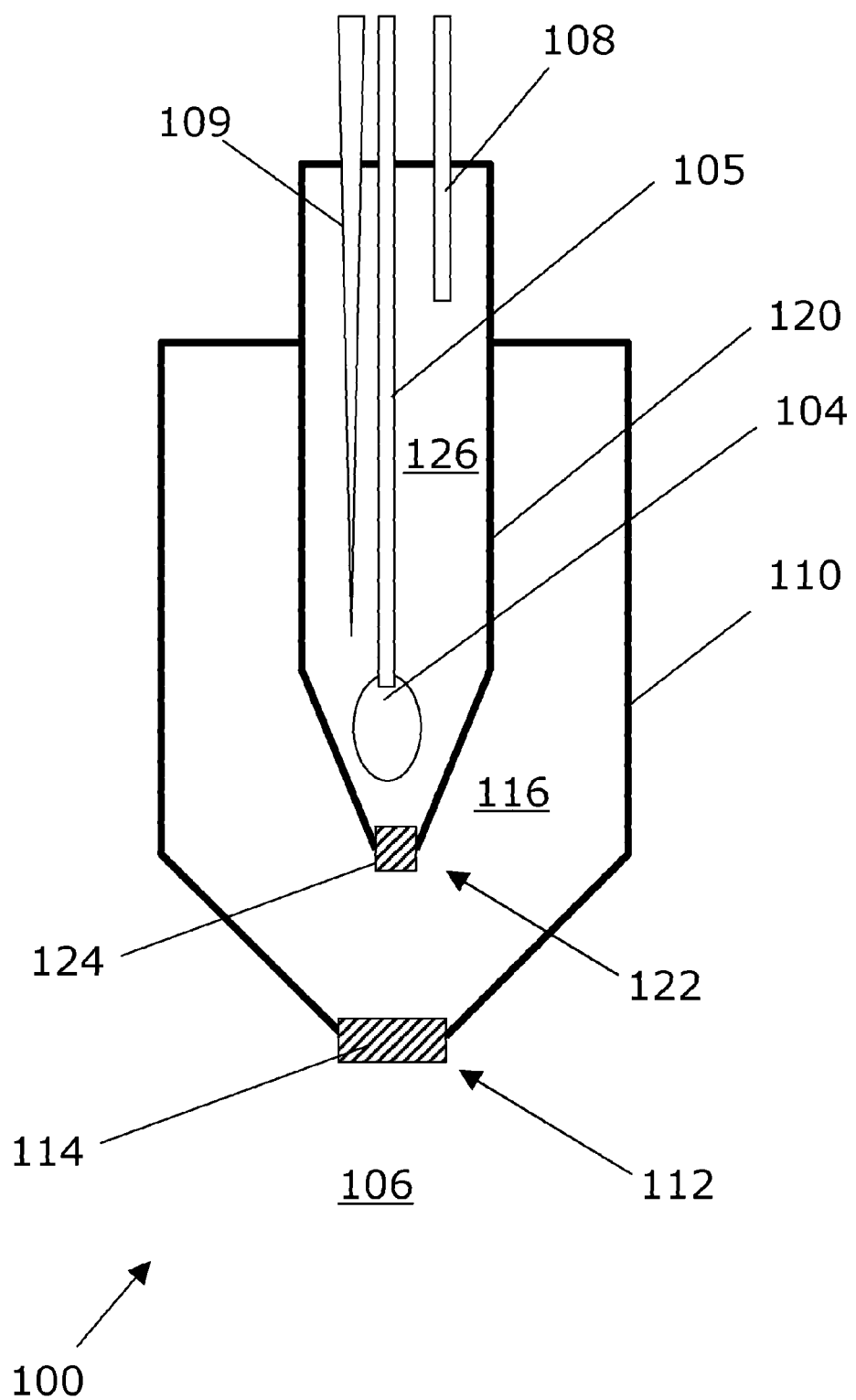
FIG. 1 is a schematic showing the structure of the sensor.

FIG. 1 shows an electrochemical sensor 100 for sensing nitrous oxide ($N_2O$) in an associated volume 106, the sensor comprising
    a primary chamber 110 having a primary opening 112 towards the associated volume 106, where a primary membrane 114 is placed in the primary opening,
    a secondary chamber 120 being placed within the primary chamber 110, such as the primary chamber being enclosed by the secondary chamber around, such as 360 degrees around a longitudinal axis of the secondary chamber, the secondary chamber 120 comprising,
    A working electrode 104,
    A reference electrode 108, which in the present embodiment comprises silver (Ag),
    A guard electrode 109, and
    An electrolyte comprising an aprotic solvent, which in the present embodiment is propylene carbonate (PC), where it is understood that electrolyte is comprising an aprotic solvent wherein an ionic compound, which in the present embodiment is tetrabutylammonium-iodide (TBA-I), is dissolved, and where the electrolyte electrically connects the reference electrode, the working electrode and the guard electrode 109,
    where the secondary chamber 120 has a secondary opening 122 towards the primary chamber 110, where a secondary membrane 124 is placed the secondary opening 122,
wherein the primary membrane 114 is permeable to nitrous oxide and is arranged so as to separate the associated volume 106 from a primary volume 116, said primary volume being within the primary chamber 110, where the secondary membrane 124 is permeable to nitrous oxide and is arranged so as to separate the primary volume 116 from the a secondary volume 126, said secondary volume being within the secondary chamber 120, wherein the primary chamber 110 comprises a means for hindering oxygen in passing into the secondary volume (126) which in the present embodiment is means for hindering a diffusion of oxygen from the associated volume 106 through the primary volume 116 and into the secondary volume 126, and wherein the working electrode 104 comprises indium (In). The working electrode 104 is electrically connected to auxiliary equipment, such as a potentiostat, via an electrical conductor 105, which may be a glass-insulated platinum wire.

In the exemplary embodiment shown in FIG. 1, the aprotic solvent is propylene carbonate, the means for hindering oxygen in passing into the secondary volume (126) comprises ascorbate, and the ionic compound is tetrabutylammonium iodide (TBA-I). Furthermore, the primary chamber has a volume 5 mL. The associated volume in this specific, exemplary embodiment comprises waste water, but it is noted that it could also have been another liquid or gas comprising $N_2O$.

Figure 2:
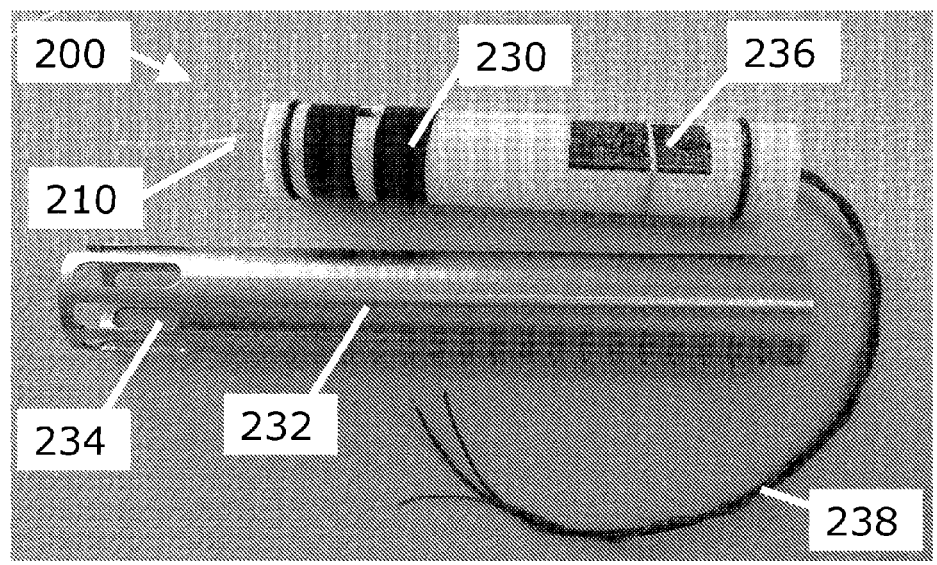
FIG. 2 is an image showing an example of a sensor with a rigid cover.

FIG. 2 shows an image of an electrochemical sensor 200, wherein the sensor further comprises a rigid cover 232 serving to protect the sensor. In the FIG. 2, the sensor 200 and the rigid cover 232 are shown displaced from each other, so as to better explain the structure. It is understood, that the sensor may be placed within the rigid cover. In the present embodiment, the rigid cover is a metallic enclosure with openings 234 serving to ensure that gas is not trapped around the sensor, and in particular not trapped in a region adjacent the primary opening. In the figure, the primary chamber 210 can also be seen, although most of the primary chamber and the secondary chamber are kept in an enclosure 230, such as an enclosure comprising a synthetic polymer, which in the present example is Nylon, such as POM-C. Furthermore, FIG. 2 shows the sensor comprises means 236 for enabling temperature compensation, wherein the means for enabling temperature compensation comprises electronically stored information which enables compensating for the effects of temperature, such as the stored information being descriptive of the influence of temperature on the output of the sensor. This information, as well as the current flowing through the working electrode, may be obtained via wiring 238, which thus enables a user to access said current, and furthermore to compensate the data obtained for the influence of temperature.

Figure 3:
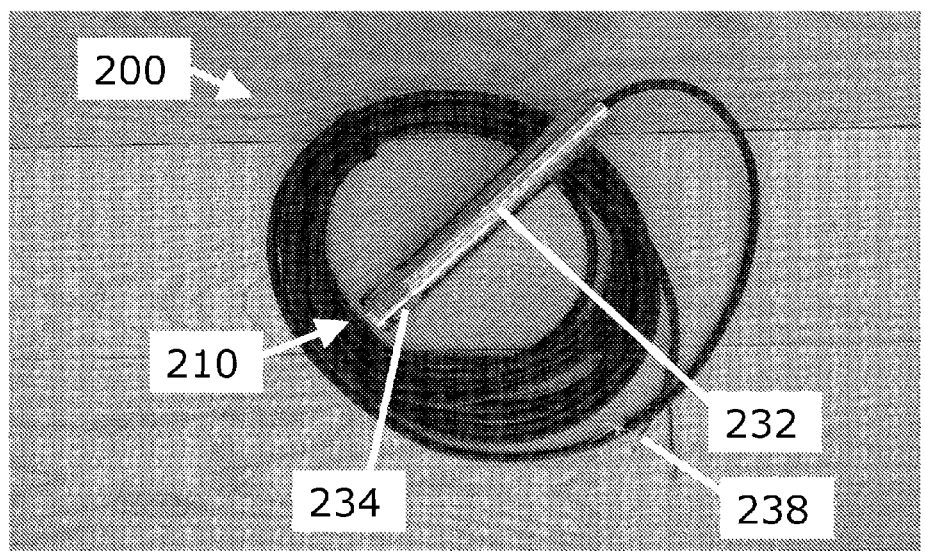
FIG. 3 is an image showing an example of a sensor with a rigid cover mounted.

FIG. 3 shows the sensor 200 also shown in FIG. 2, but in FIG. 3 the rigid cover 232 is mounted, so that that the first chamber 210 and the second chamber cannot contact planar surfaces.

Figure 4:
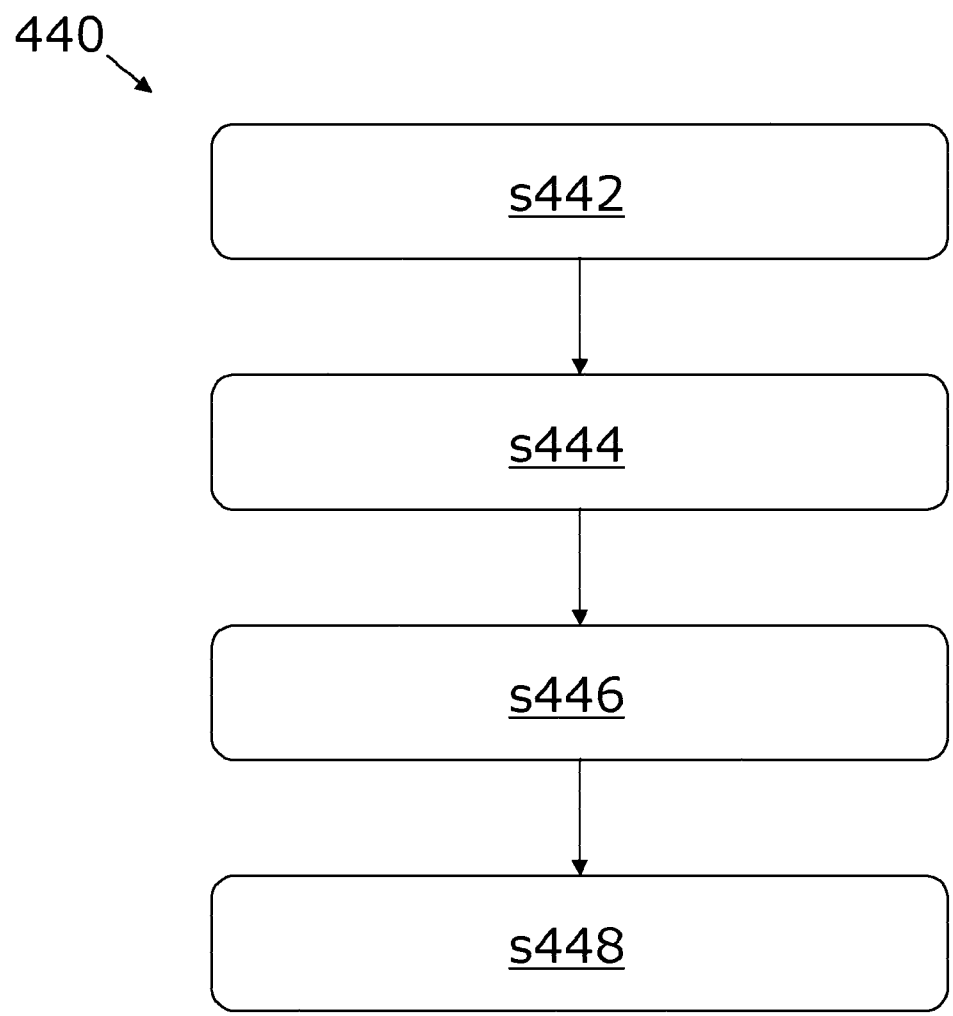
FIG. 4 is a flow-chart of a method according to the invention.

FIG. 4 shows a method 440 for electrochemically sensing nitrous oxide (N2O) in an associated volume, the method comprising
  providing s442 a primary chamber having a primary opening towards the associated volume, where a primary membrane is placed in or around the primary opening,
  providing s444 a secondary chamber being placed adjacent the primary chamber or partially surrounded by the primary chamber, the secondary chamber comprising,
    a reference electrode,
    a working electrode, and
    an electrolyte comprising an aprotic solvent, such an aprotic solvent wherein an ionic compound is dissolved, where the electrolyte electrically connects the reference electrode and the working electrode,
  where the secondary chamber has a secondary opening towards the primary chamber, where a primary membrane is placed in or around the secondary opening,
  wherein the primary membrane is permeable to nitrous oxide and is arranged so as to separate the associated volume from a primary volume, said primary volume being within the primary chamber,
  wherein the secondary membrane is permeable to nitrous oxide and is arranged so as to separate the primary volume from the secondary volume, said secondary volume being within the secondary chamber,
  where the primary chamber comprises means for hindering oxygen in passing into the secondary volume (126), and
  wherein the working electrode comprises indium (In), the method further comprising reducing s446 the nitrous oxide at the working electrode and measuring s448 the corresponding current flowing through the working electrode.

Examples

Test on the Use of Different Electrolytes

Different types of electrolytes have been used so as to evaluate their influence on the performance of the electrochemical sensor.

The electrolyte used for testing the performance of the electrochemical sensor comprises an aprotic solvent and an ionic compound therein dissolved, so as to electrochemically connect the reference electrode (RE) and the working electrode (WE) used.

Since the metal present in the working electrode is sensitive to hydrogen element reduction to hydrogen gas, the use of an aprotic solvent has the main advantage of avoiding this side reaction and thus enhancing the signal to noise ratio towards the detection of the desired species.

The four different ionic compounds dissolved in the aprotic solvent used for the tests were:
  Tetra-butyl-ammonium-Iodide (TBA-I);
  Tetra-butyl-ammonium-Chlorate (TBA-Cl);
  Tetra-butyl-ammonium-Flouroborate (TBA-BF$_4$); and
  Tetra-butyl-ammonium-Perchlorate (TBA-ClO$_4$).

In all the examples the second chamber was filled with a solution of the corresponding TBA salt in a concentration 0.3 M using propylene carbonate (PC) as solvent. The electrochemical sensor was then exposed to a solution $N_2O$ in a concentration of 100 µM. For each different TBA salt used the test was repeated on three electrochemical sensors. The principal performance characteristics, the level of the baseline signal and the sensitivity to the $N_2O$ were described as a function of the polarization voltage level. The optimal polarization voltage for each TBA salt was defined as the lowest level where a stable $N_2O$ response was found. The results are summarized in Table 1.

TABLE 1

|  | TBA-I | TBA-Cl | TBA-BF$_4$ | TBA-ClO$_4$ |
|---|---|---|---|---|
| Optimal voltage level (V) | −0.8 | −1.0 | −1.1 | −1.4 |
| Baseline signal (pA) | 4.1 ± 2.6 | 5.7 ± 1.3 | 3.2 ± 2.0 | 8.8 ± 4.5* |
| Response (pA/100 µM $N_2O$) | 302 ± 77 | 319 ± 29 | 342 ± 41 | 299 ± 57 |

*One of the three sensors had abnormaly high baseline signal

It was found that the performance of the electrochemical sensor employing the different salts was similar. Thus comparable good results may be obtained using any one of the tested salts in terms of baseline signal properties and $N_2O$ sensitivity.

It should be noticed that electrochemical sensors using electrolyte with different salts needs different level of polarization. The optimal polarization level ranged from −0.8V to −1.4V.

Test on the Use of Different Metals as Active Components of the WE

The suitability of four different metals as the reactive surface component of the WE in the $N_2O$ sensor was evaluated. These metals were Indium (In), Silver (Ag), Palladium (Pd) and Platinum (Pt). In all the examples the second chamber was filled with a solution of TBA-I in a concentraction 0.3 M using propylene carbonate (PC) as solvent. The primary volume was filled with a solution of ascorbate with a concentration of 0.75 M. The electrochemical sensor was then exposed to a solution $N_2O$ in a concentration of 100 µM. The solution also comprised oxygen (air saturated, ~275 µM $O_2$)

For each different metal used the test was repeated on three electrochemical sensors. The principal performance characteristics, the level of the baseline signal and the sensitivity to the $N_2O$ were described as a function of the polarization voltage level. The optimal polarization voltage for each metal was defined as the lowest level where a stable $N_2O$ response was found. The results are summarized in Table 2.

TABLE 2

|  | In | Ag | Pd* | Pt |
|---|---|---|---|---|
| Optimal voltage level (V) | −0.8 | −0.8 | −0.8 | ** |
| Baseline signal (pA) | 4.1 ± 2.6 | 57 ± 45 | 190 ± 110 | 200-5000 |
| Response (pA/100 µM $N_2O$) | 302 ± 77 | 314 ± 23 | 270 ± 43 | 0 |

*Data are based on the results of two sensors
** An optimal voltage level could not be identified for Platinum.

Figure 5:
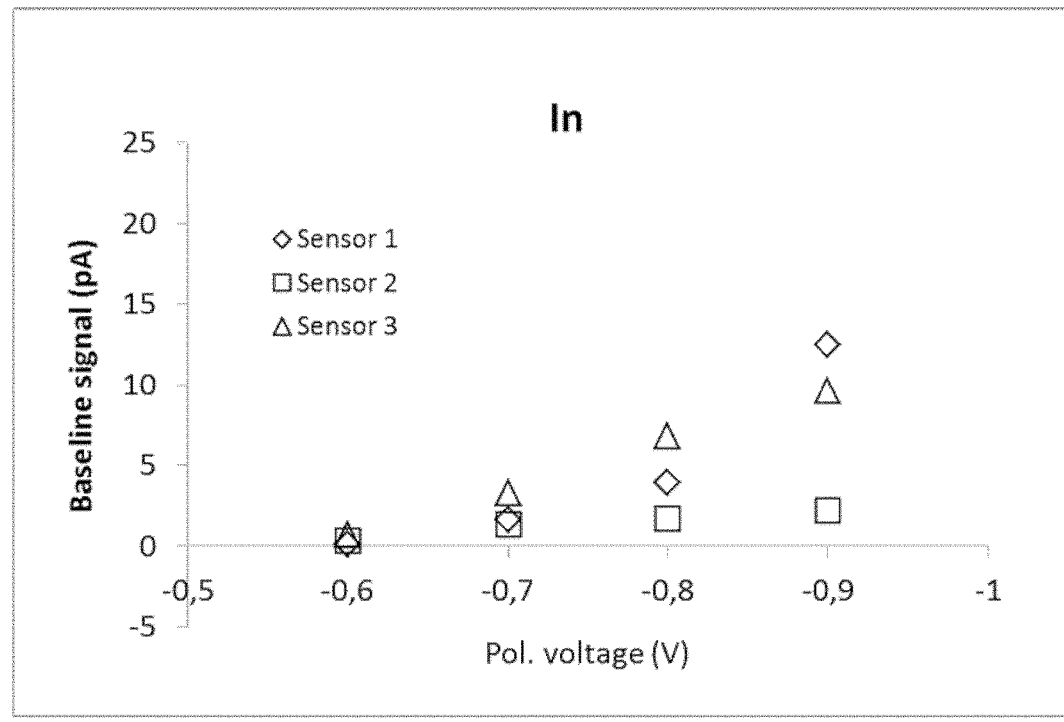
Figure 6:
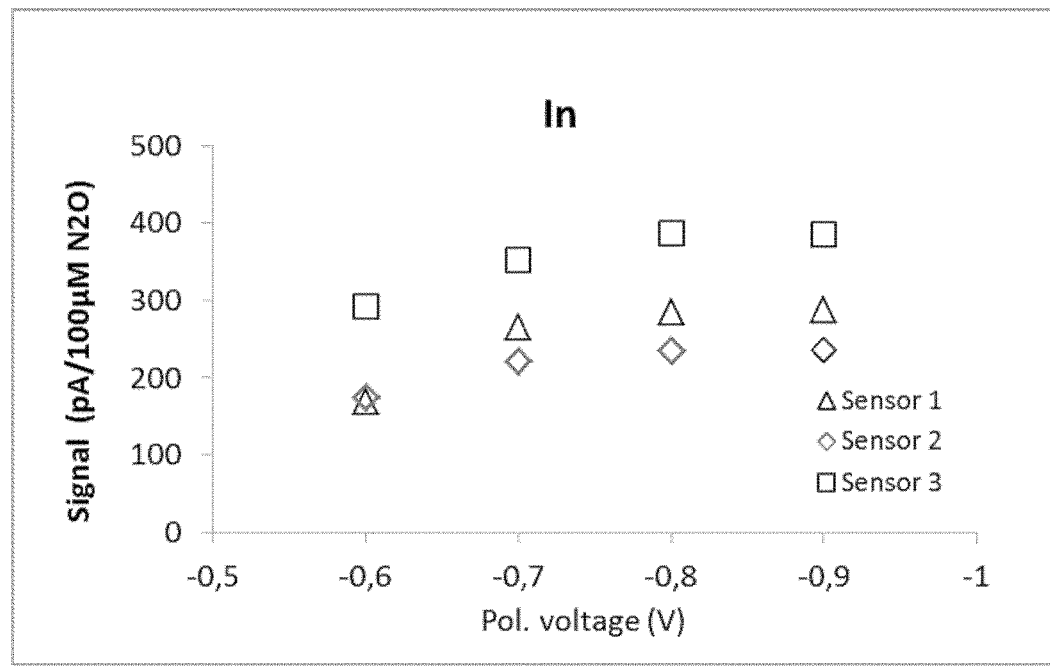

From table 2, FIG. 5 and FIG. 6 it can be clearly seen that the electrochemical sensor having as active component of the WE the metal Indium (WE/In) shows the best performance.

Indeed WE/In has the lowest baseline signal and one of the highest sensitivities to $N_2O$ when compared to electrochemical sensors employing as active component of the WE other metals such as Ag, Pd and Pt. Furthermore the baseline signal level of WE/In is lower than 10 pA, and coupled to a response in the order of 300 pA/100 μM of $N_2O$ provides a very high signal to noise ratio.

Figure 7:
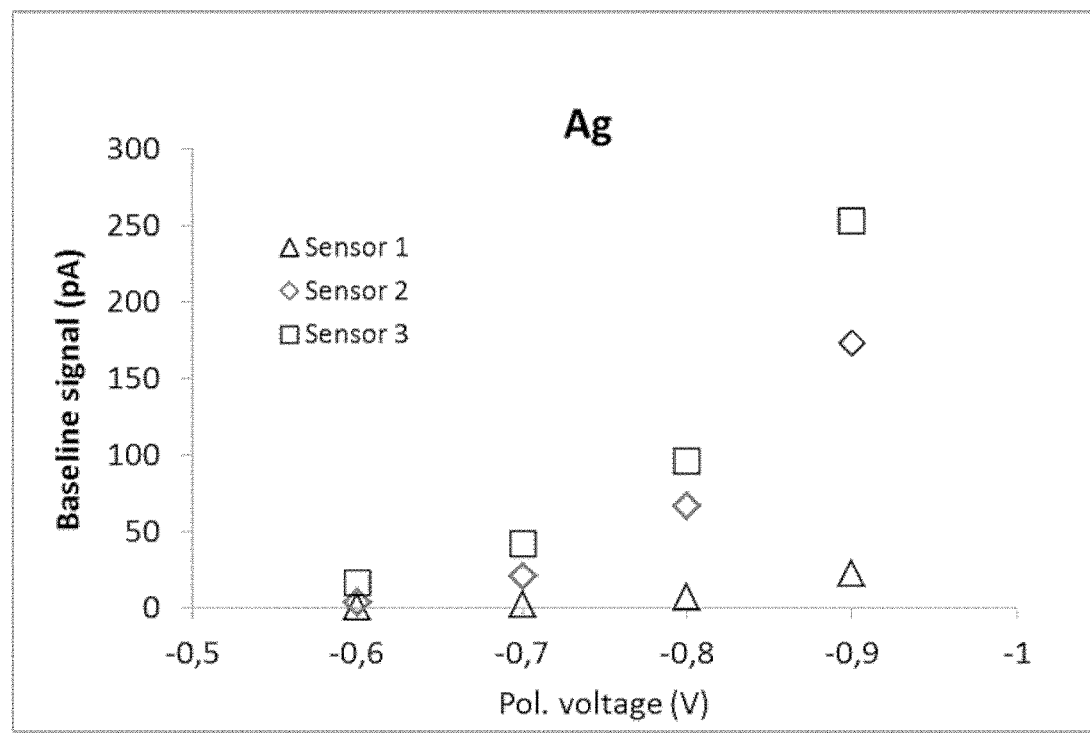
FIG. 7 is plot of the baseline signal (pA) as a function of the polarization voltage (V) for an electrochemical sensor when the working electrode comprises Ag.
Figure 8:
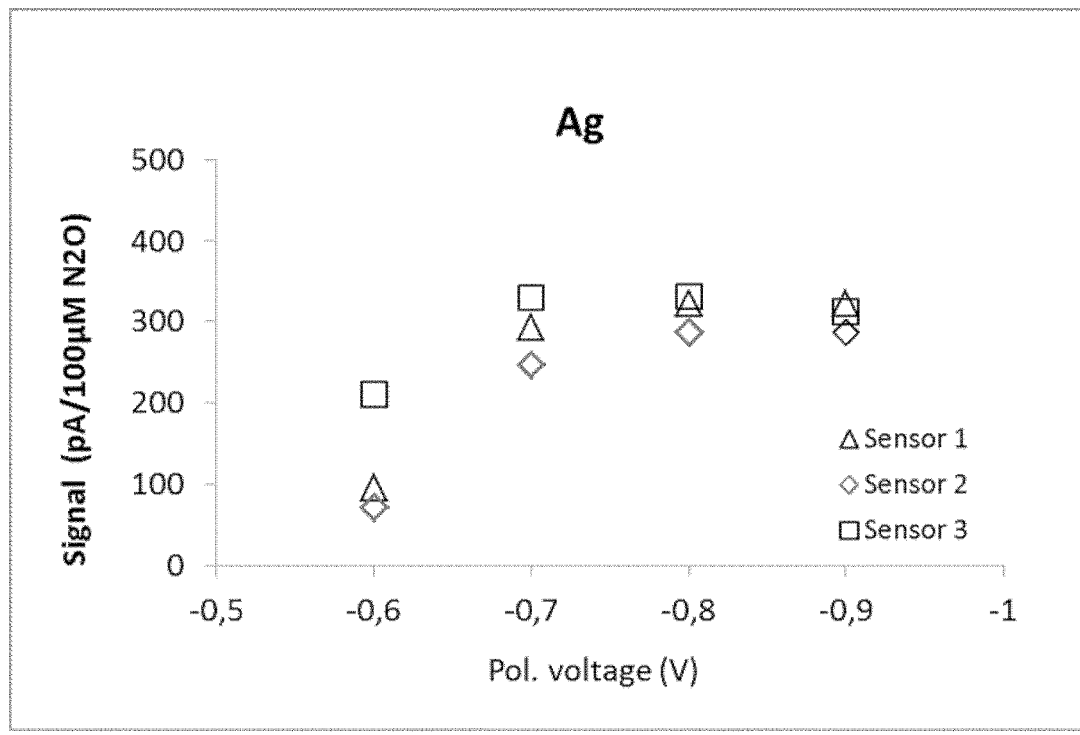
FIG. 8 is plot of the signal in response to the exposure of $N_2O$ (PA/100 μM $N_2O$) as a function of the polarization voltage (V) for an electrochemical sensor when the working electrode comprises Ag.

As shown in table 2, FIG. 7 and FIG. 8 an electrochemical sensor wherein the WE comprises Ag (WE/Ag) also has a good response to $N_2O$, however it also has a relatively high (57 pA) and varying (±45 pA) level of the base line. Thus, due to the high base line, the performance of WE/Ag is inferior to the one of WE/In. The electrochemical sensor comprising Pd in the working electrode showed a very high baseline signal, thus despite a good sensitivity to $N_2O$ it is not a good candidate for a good $N_2O$ electrochemical sensor. When Pt was used in the WE, the sensor showed no analytic sensitivity within the tested range.

Figure 9:
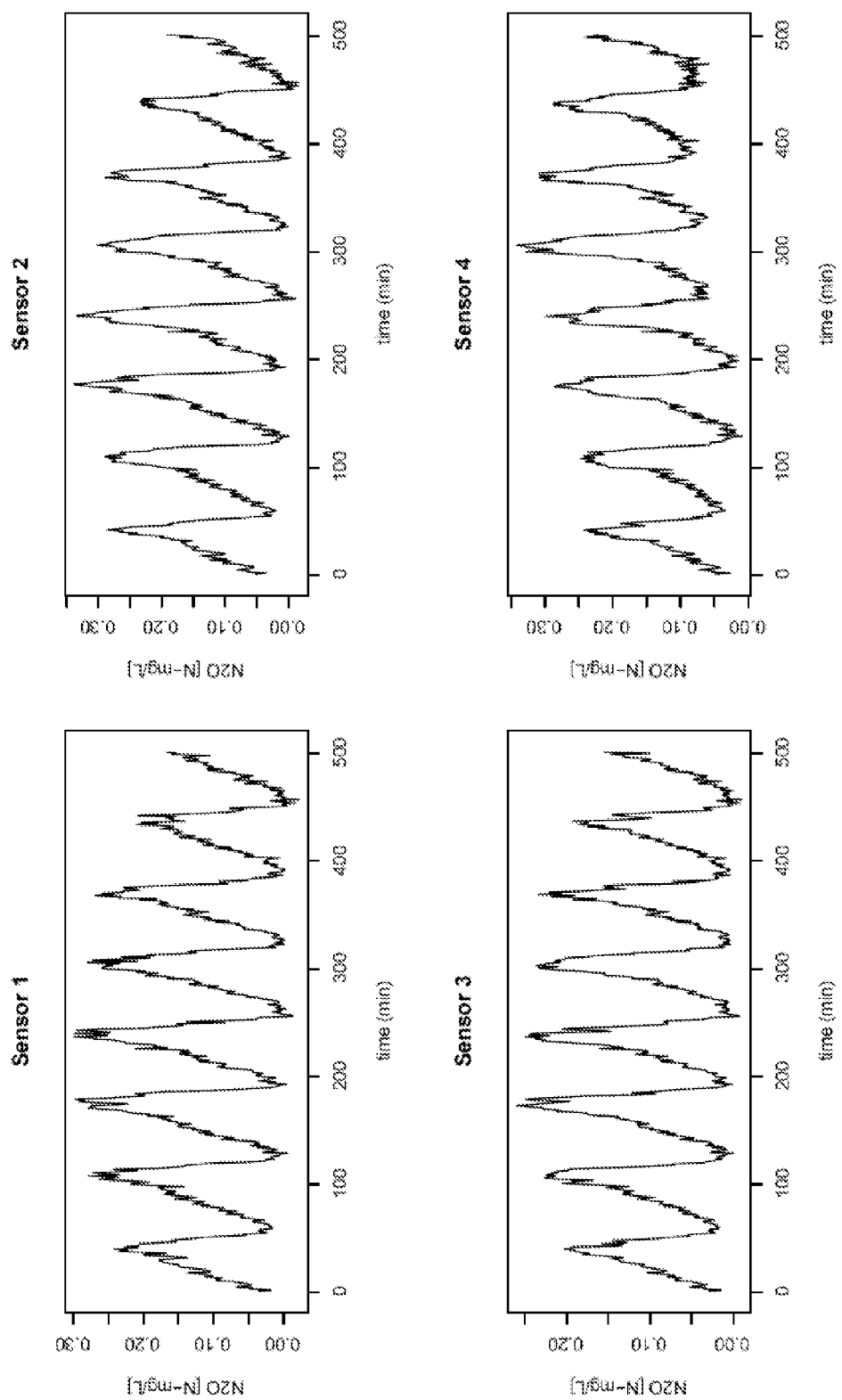
FIG. 9 shows the real-time response of sensors exposed to $N_2O$.

FIG. 9 shows the real-time response of different sensors exposed to $N_2O$ in a wastewater treatment process. Within a full-scale activated sludge plant with a high organic load from an industrial wastewater treatment facility there was installed 4 $N_2O$ sensors distributed in a tank of volume 4.200 $m^3$ which were operated under alternating aerobic/anaerobic conditions. Continuous measurements during both nitrification and denitrification as time series measurements (i.e., corresponding sets of time and $N_2O$ concentration) were obtained from the sensors. During the aeration the airflow was maximum 1.6 $m^3$/hr for each of 4 aeration fields. The figure shows that the sensor may be used for can be reliably monitoring, such as reliably monitoring nitrous oxide, such as monitoring nitrous oxide as a function of time in wastewater in a wastewater treatment facility. The monitoring of nitrous oxide may span long periods of time such as more than 60 minutes, such as more than 120 minutes, such as more than 180 minutes, such as more than 240 minutes, such as more than 300 minutes, such as more than 360 minutes, such as more than 420 minutes, such as more than 480 minutes, such as more than 500 minutes.

Figure 10:
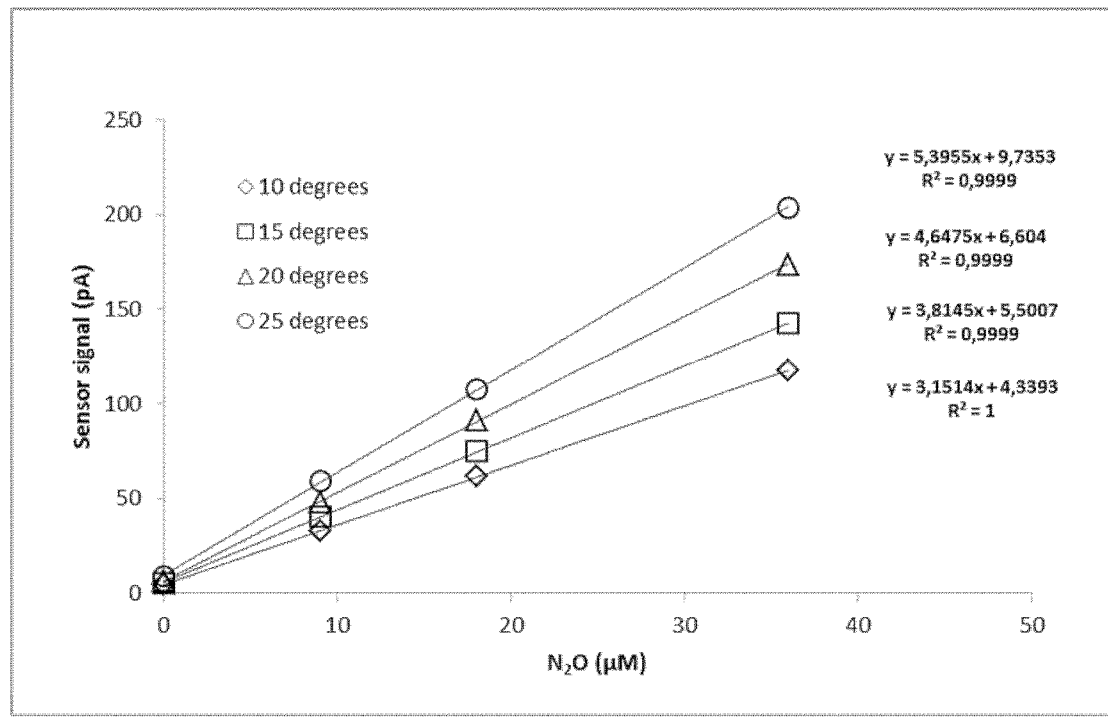
FIG. 10 shows an example of sensor calibration data.

FIG. 10 shows an example of sensor calibration data. The data illustrates the perfectly linear response of the $N_2O$ sensor technology. The data further illustrates and exemplifies the effect of temperature on the sensor signal response, since the four curves are obtained at different temperatures of 10, 15, 20, 25 degrees Celcius. These calibration curves also serve to illustrate, that the effect of temperature can be measured, which in turn enables compensating for temperature effects. The shown calibrations were performed in a water environment and in a concentration range between 0 to 36 μM $N_2O$.

Figure 11:
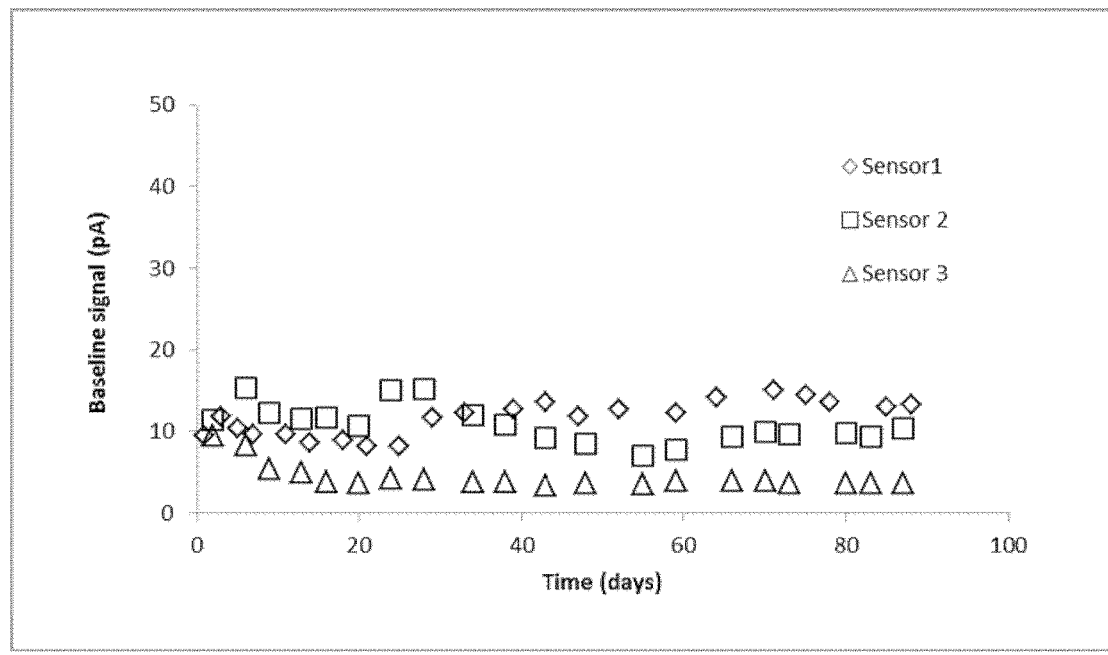
FIGS. 11-12 show long-term stability of the sensor baseline signal and the $N_2O$ response.
Figure 12:
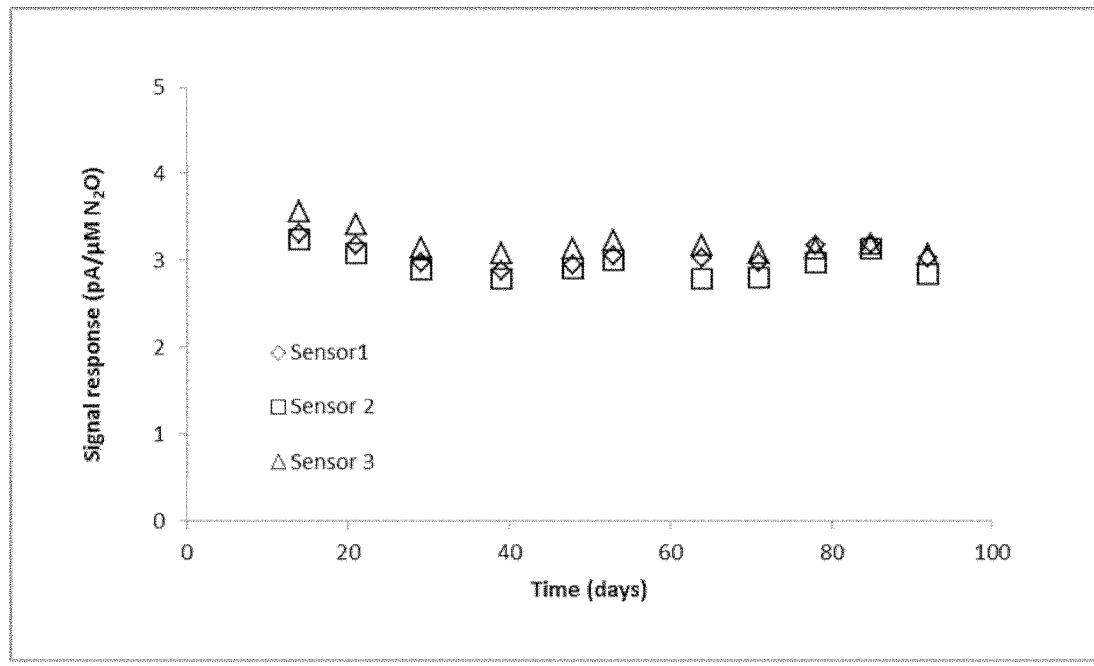

FIGS. 11-12 show long-term stability of the sensor baseline signal and the N2O response. The two figures describe the stability of two important features of the sensor: (1) The baseline signal in FIG. 11 and (2) the response signal in FIG. 12. The presented data in FIGS. 11-12 cover a three months period and are shown for three sensors. The baseline signals are recorded in air at room temperature while the sensor response data were tested in the water phase at room temperature (about 21.5 degrees Celcius). FIGS. 11-12 serve to illustrate, that the sensor is stable over extended periods of time, which implies that the sensor is amenable for, e.g., long term monitoring.

FIG. 11 shows stability data for the sensor baseline current during a 90 days period exemplified for 3 $N_2O$ sensors.

FIG. 12 shows stability of the sensor response during a 90 days period exemplified for 3 $N_2O$ sensors.

The $N_2O$ sensor was tested for measurements of trace $N_2O$ levels in the gas phase. In two separate experiments, the sensor signal response to $N_2O$ additions of 6 ppm and 25 ppm, respectively, was continuously monitored in a temperature controlled environment. In both tests a linear $N_2O$ response was present and the analytical sensitivity (AS) was determined to be 0.2-0.3 pA/ppm $N_2O$.

The noise amplitude (NA), such as the Root-Mean-Squared (RMS) noise, for the present nitrous oxide sensor is estimated to be 0.1 pA (measured at room temperature and without electric shielding, where the electric shielding may be understood to be external electric shielding).

The detection limit (DL) for the nitrous oxide sensor (at room temperature and without electric shielding), may be determined as follows:

$$DL_{gas} = (2*NA)/AS$$
$$= (2*0.1 \text{ pA})/(0.3 \text{ pA/ppm})$$
$$= 1 \text{ ppm}$$

It is understood, that the detection limits in liquid and gaseous phases correspond to each other, since the sensor responds to the partial pressure (not concentration), and there is a linear correspondence between the partial pressure in the gaseous phase and the concentration in liquid under equilibrium conditions.

For exemplary purposes, the detection limit in liquid (at room temperature and without electric shielding) may be estimated as follows:

$$DL_{liquid} = (2*NA)/AS$$
$$= (2*0.1 \text{ pA})/(302 \text{ pA/100 μm})$$
$$= (2*0.1 \text{ pA})/(0.3 \text{ pA/100 nm})$$
$$= 70 \text{ nm}$$

Figure 13:
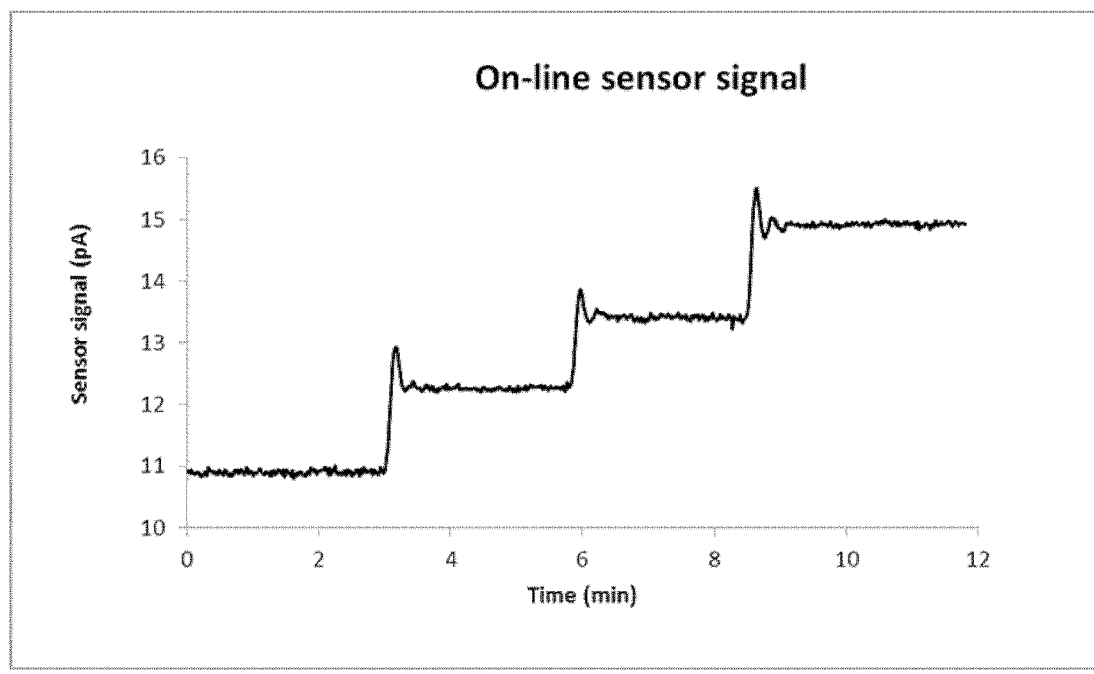
FIG. 13 shows test data for $N_2O$ sensor during gas phase measurements.
Figure 14:
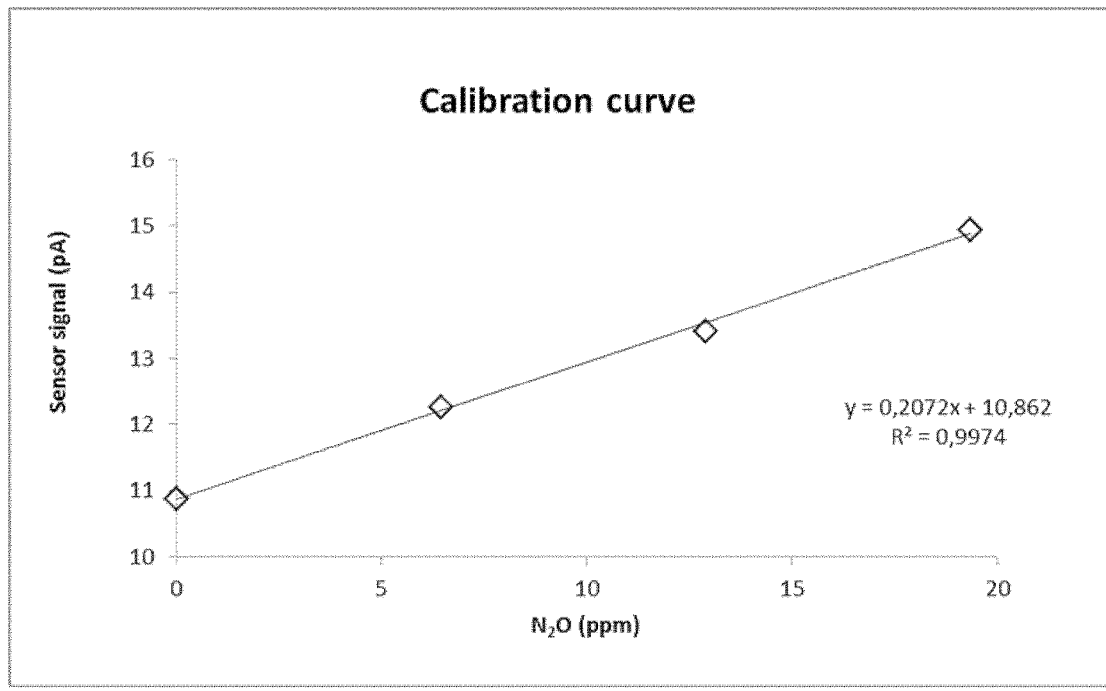
FIG. 14 shows sensor calibration curve corresponding to the data in FIG. 13.

FIG. 13 shows test data for $N_2O$ sensor during gas phase measurements, by showing on-line sensor response to several additions of about 6 ppm $N_2O$ FIG. 14 shows the sensor calibration curve corresponding to the experiment shown in FIG. 13.

Figure 15:
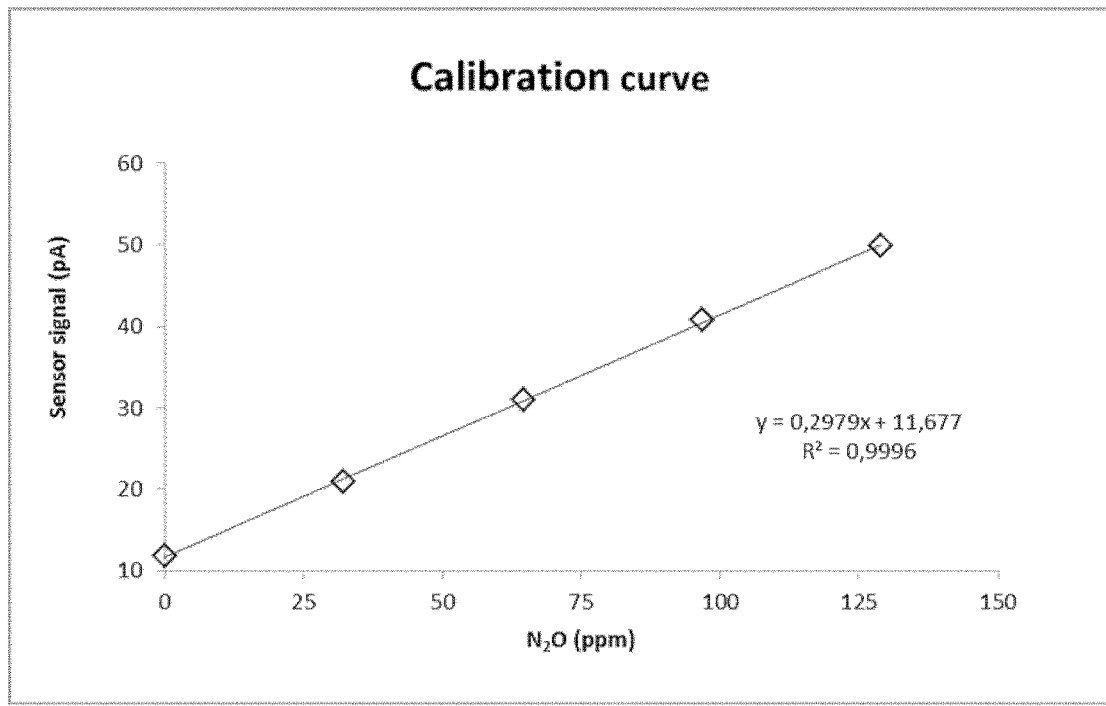
FIG. 15 shows a sensor calibration curve for test data for an $N_2O$ sensor during gas phase measurements.

FIG. 15 shows a sensor calibration curve for test data for an $N_2O$ sensor during gas phase measurements, wherein the test data corresponded to several additions of about 25 ppm $N_2O$.

FIGS. 16-20 show an enclosure suited for holding the electrochemical sensor, such as the enclosure being an inner tubing, which may be enclosed by an outer tubing such as the rigid cover.

Figure 16:
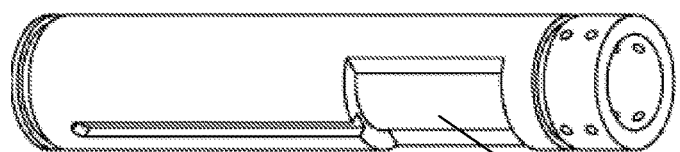
FIGS. 16-20 show an enclosure suited for holding the electrochemical sensor.
Figure 17:
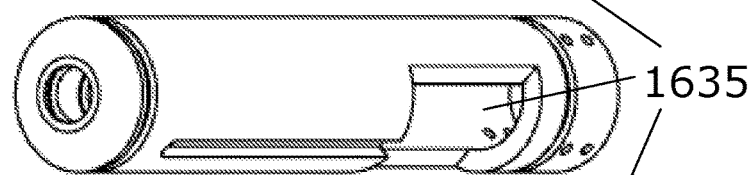

FIGS. 16-17 show perspective view of the enclosure, where hole 1635 is shown, which hole may, for example hold electronics for storing data values enabling temperature compensation.

Figure 18:
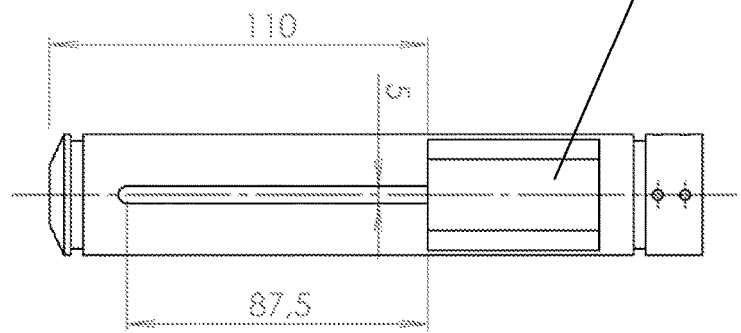
Figure 19:
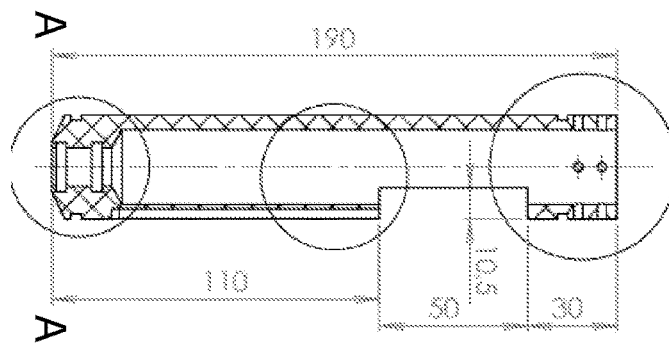
Figure 20:
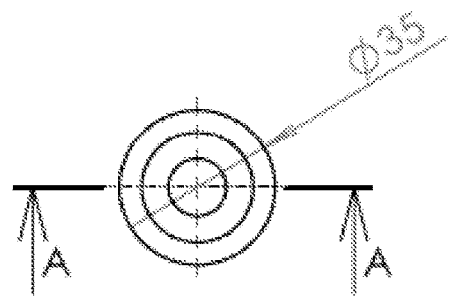

FIGS. 18-20 show drawings with exemplary dimensions marked, the dimensions being given in millimeters (mm).

FIG. 18 shows a side view.

FIG. 19 shows a cross-sectional view.

FIG. 20 shows an end view.

Figure 21:
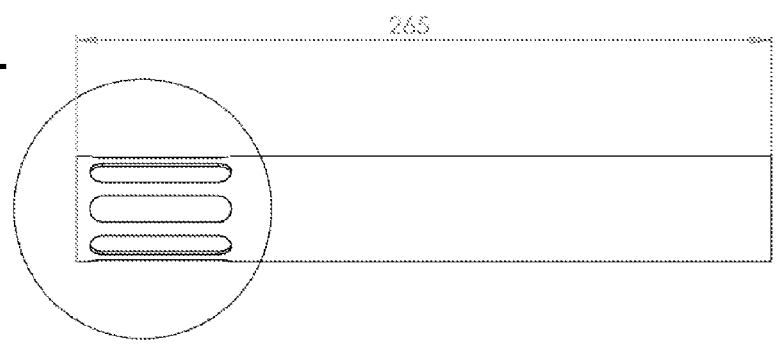
FIGS. 21-22 show a rigid cover.
Figure 22:
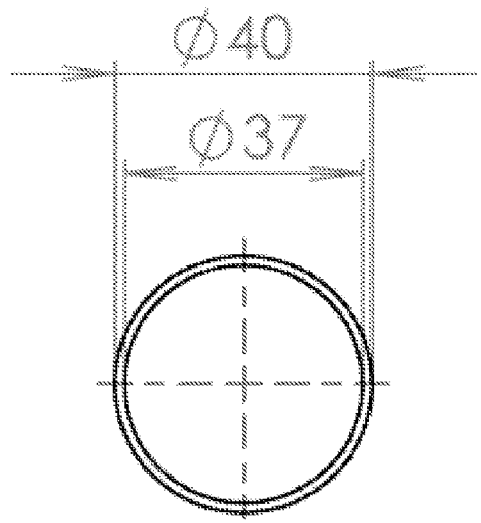

FIGS. 21-22 show a rigid cover, such as outer tubing for mounting on the inner tubing of FIGS. 16-20 (which in turn was arranged for mounting on the sensor)). Both figures show drawings with exemplary dimensions marked, the dimensions being given in millimeters (mm).

FIG. 21 show a side view.

FIG. 22 show an end view.

Figure 23:
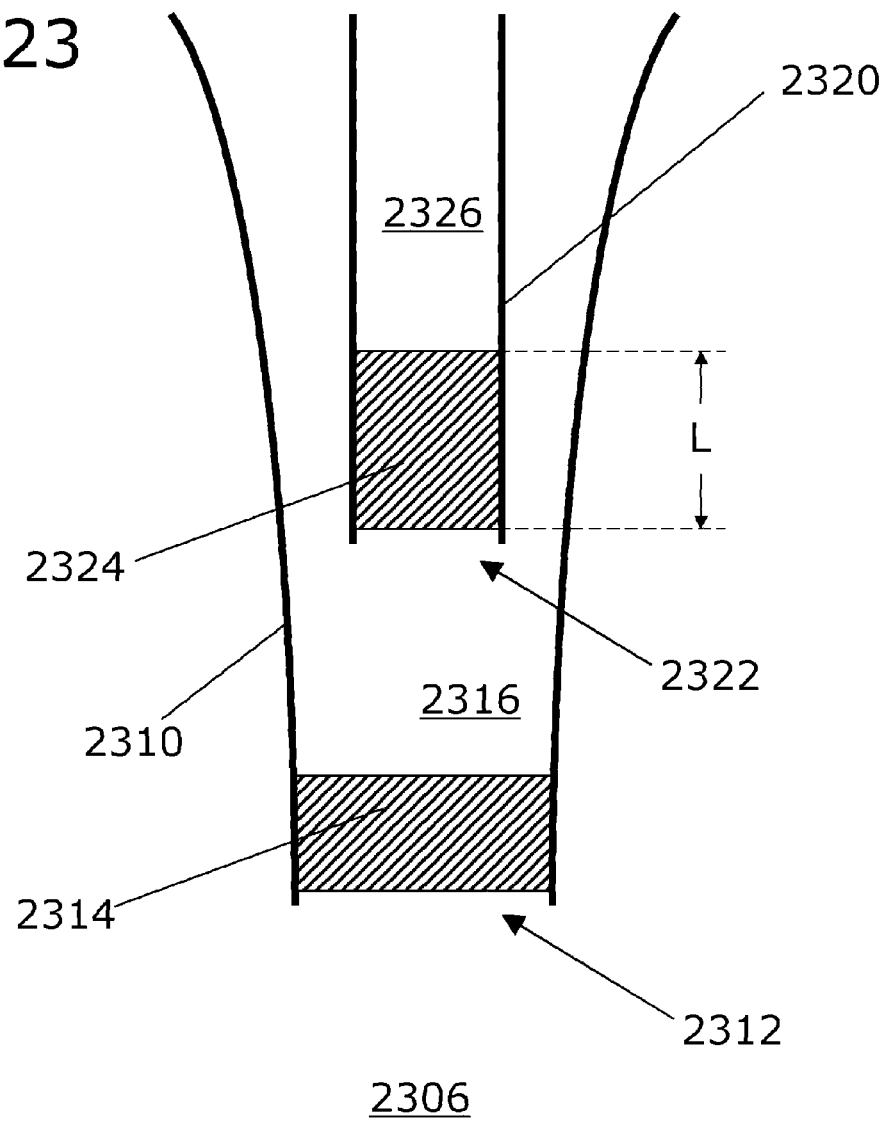
FIG. 23 is a schematic drawing showing the secondary opening membrane length (L)

FIG. 23 is a schematic showing the secondary opening membrane length (L). More particularly, the figure shows a portion of a sensor (similar to the sensor in, e.g., FIG. 1), i.e., an electrochemical sensor for sensing nitrous oxide ($N_2O$) in an associated volume 2306, the sensor comprising a primary chamber 2310 having a primary opening 2312 towards the associated volume 2306, where a primary membrane 2314 is placed in the primary opening, a secondary chamber 2320 being placed within the primary chamber 2310, such as the primary chamber being enclosed by the secondary chamber around, such as 360 degrees around a longitudinal axis of the secondary chamber, where the secondary chamber 2320 has a secondary opening 2322 towards the primary chamber 2310, where a secondary membrane 2324 is placed in the secondary opening 2322, wherein the primary membrane 2314 is permeable to nitrous oxide and is arranged so as to separate the associated volume 2306 from a primary volume 2316, said primary volume being within the primary chamber 2310, where the secondary membrane 2324 is permeable to nitrous oxide and is arranged so as to separate the primary volume 2316 from the a secondary volume 2326, said secondary volume being within the secondary chamber 2320, and wherein the figure furthermore indicates the secondary opening membrane length L, which corresponds in the figure to the minimum length which an entity, such as an analyte (such as $N_2O$) and/or water vapour, originally placed in the primary chamber would need to travel through the secondary opening membrane 2324 in order to get into the secondary chamber through the secondary opening membrane. In the figure the primary chamber and the secondary opening and the secondary opening membrane are arranged so that said entity can realistically only pass from the primary chamber to the secondary chamber through the secondary opening membrane, since the primary and secondary chamber are otherwise separated by the boundary walls of the primary chamber which are of glass which cannot be penetrated by the entity, such as $N_2O$ or $H_2O$.

The correlation between secondary opening membrane length and sensor baseline signal of embodiments of electrochemical sensors for sensing nitrous oxide has been examined, and results are shown in FIGS. 24-30.

Four different versions of an electrochemical sensor for sensing nitrous oxide with secondary opening membrane lengths of 25 µm, 50 µm, 100 µm and 150 µm were prepared, and for each version four to ten sensors were used during the test. The level of the baseline signal was followed for at least 60 days or until the time where the sensor signal had increased to more than a set threshold level of pA. The polarization voltage, i.e., the voltage applied between reference electrode and working electrode was −0.8 V. In all the examples the second chamber was filled with a solution of TBA-I in a concentration 0.3 M using propylene carbonate (PC) as solvent.

The experimental data shows that there is a surprising, yet strong correlation between secondary opening membrane length and (1) the size and variability of the sensor baseline signal, and (2) the sensor lifetime where a low baseline signal (<15 pA) can be retained (it may be understood that short-term spikes in the data, such as signal levels exceeding 15 pA for a short period of time, such as for a period of less than 10 seconds, such as less than 1 second, such as less than 0.1, second may be excluded).

The increase of secondary opening membrane length dramatically improves the sensor lifetime. For example, all sensors prepared with a 150 µm secondary opening membrane length demonstrated a lifetime of more than 180 days whereas sensors with a secondary opening membrane length of 25 µm showed an average lifetime of 8 days. Sensors with a long secondary opening membrane length, such as 150 µm) have on average a markedly lower baseline level and equally demonstrated significantly lower baseline variation.

By 'baseline variability' may be understood a measure of how stretched or spread out a distribution describing the baseline level for a population of sensors would be. A large variability thus indicates that the baseline level may vary a lot across the population of sensors, whereas a group of sensors showing a low baseline variability would have more similar baseline values.

The increase in the sensor baseline signal over time, either gradually or more abruptly, may be caused by water interference, such as being due to an increased reduction of gaseous water at the cathode surface. The rise in the baseline may be seen as problematic as sensors with a higher baseline in general may be more unstable (noisy) and also more sensitive to temperature fluctuations in the measuring environment. The elevated baseline therefore reduces the precision of the $N_2O$ measurement and overall decreases the detection limit of the technology, both potentially critical properties for the $N_2O$ sensing technology where accurate measurements of low $N_2O$ levels may be required.

The mechanism whereby the application of longer secondary opening membrane lengths may be beneficial for increasing life time and/or reducing baseline signal may be explained as follows: By having a longer secondary opening membrane length it may be possible to reduce an amount of water vapor that reaches the sensor cathode, since the water vapor will have to travel further in order to move from the primary chamber to the secondary chamber. A shorter secondary opening membrane length may result in a steeper water vapor gradient across the secondary opening membrane. It may be understood, that the present inventors have made the insight, that a longer membrane may be beneficial for avoiding water entry into the secondary chamber, and may thus be beneficial for detection or measurement of any analyte within the group of analytes where interference from water may be a problem (such as where interference from water may result in any one of increase of baseline level, increase in noise level, reduction of lifetime), such as $N_2O$, H2, NO, $CO_2$, $CH_4$ and/or $N_2$. It may be understood, that the present inventors have made the insight, that a longer membrane may be beneficial for avoiding water entry into the secondary chamber, and may thus be beneficial for detection and/or measurement of any analyte within the group of analytes where the polarization level that is to be applied for measuring said analyte with a given sensor, such as sensor constructed with a given electrolyte and metal surface configuration (such as for a given working electrode material), is a polarization level where active water splitting takes place, such as where active water splitting takes place to a degree which under practical circumstances degrades sensor performance.

Figure 24:
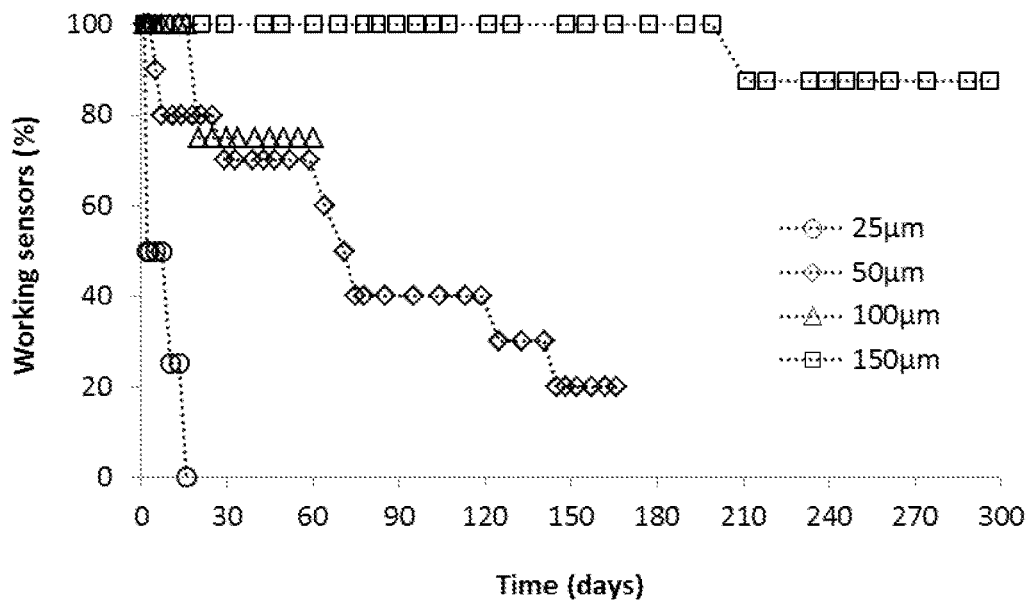
FIG. 24 shows percentage of sensors working dependent on time and secondary opening membrane length (L) for nitrous oxide sensors constructed with secondary opening membrane lengths of 25 μm, 50 μm, 100 μm and 150 μm, respectively.

FIG. 24 shows percentage of sensors working dependent on time and secondary opening membrane length (L) for nitrous oxide sensors constructed with secondary opening membrane lengths of 25 µm, 50 µm, 100 µm and 150 µm, respectively.

Figure 25:
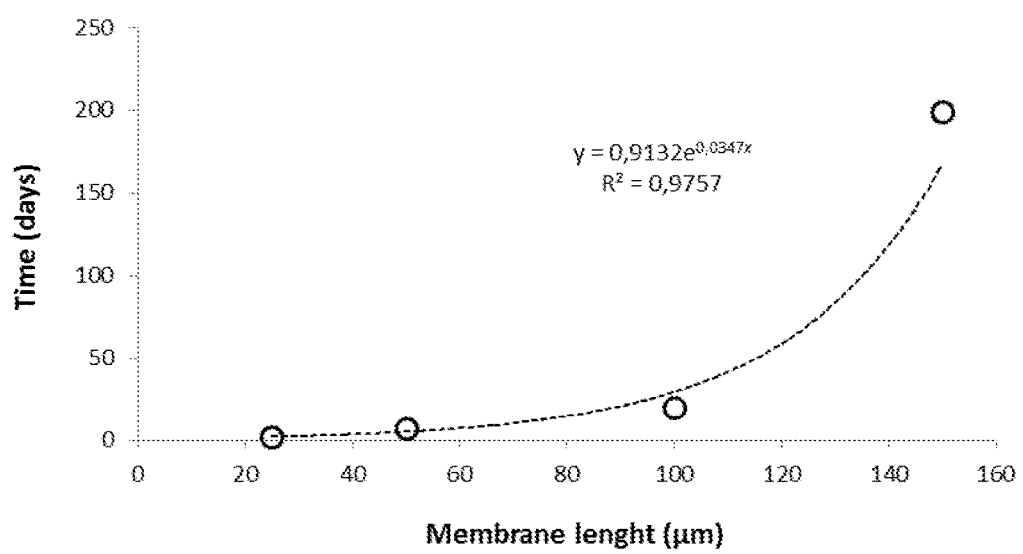
FIG. 25 shows the relationship between between secondary opening membrane length and lifetime where 100% of the sensors have a baseline <15 pA.

FIG. 25 shows the relationship between between secondary opening membrane length and lifetime where 100% of the sensors have a baseline <15 pA.

Figure 26:
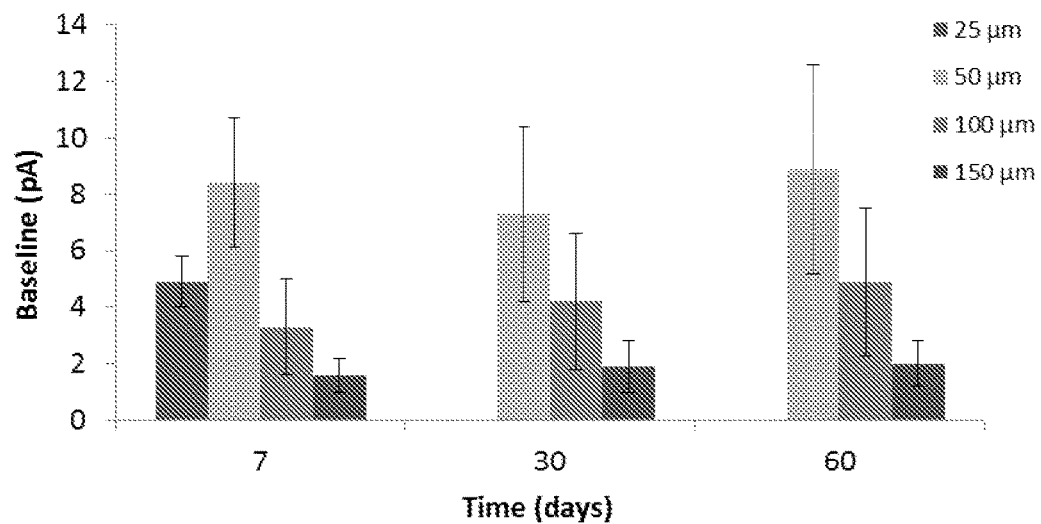
FIG. 26 shows average level of the baseline signal for sensors constructed with secondary opening membrane lengths of 25 μm, 50 μm, 100 μm and 150 μm, after 7, 30 and 60 days of operation.

FIG. 26 shows average level of the baseline signal for sensors constructed with secondary opening membrane lengths of 25 μm, 50 μm, 100 μm and 150 μm, after 7, 30 and 60 days of operation. Error bars show standard deviations. Sensors with a baseline >15 pA are not included.

Figure 27:
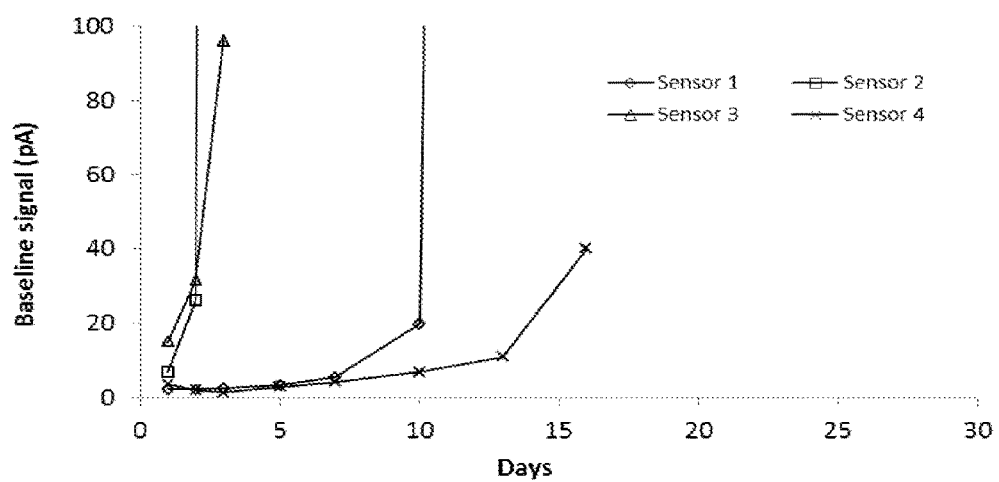
FIG. 27 shows sensor baseline signal as a function of time for sensors constructed with a secondary opening membrane length of 25 μm.

FIG. 27 shows sensor baseline signal as a function of time for sensors constructed with a secondary opening membrane length of 25 μm.

Figure 28:
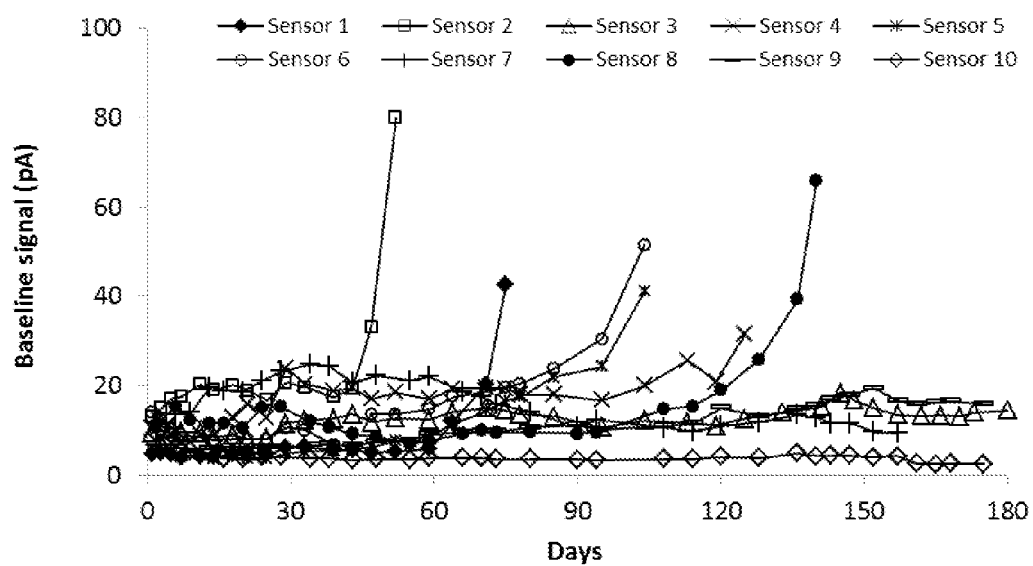
FIG. 28 shows sensor baseline signal as a function of time for sensors constructed with a secondary opening membrane length of 50 μm.

FIG. 28 shows sensor baseline signal as a function of time for sensors constructed with a secondary opening membrane length of 50 μm.

Figure 29:
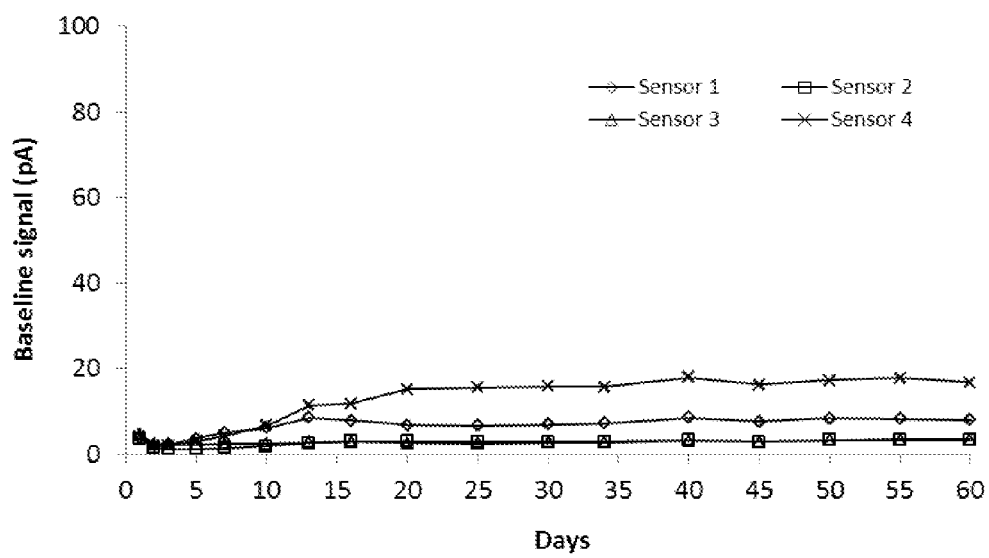
FIG. 29 shows sensor baseline signal as a function of time for sensors constructed with a secondary opening membrane length of 100 μm.

FIG. 29 shows sensor baseline signal as a function of time for sensors constructed with a secondary opening membrane length of 100 μm.

Figure 30:
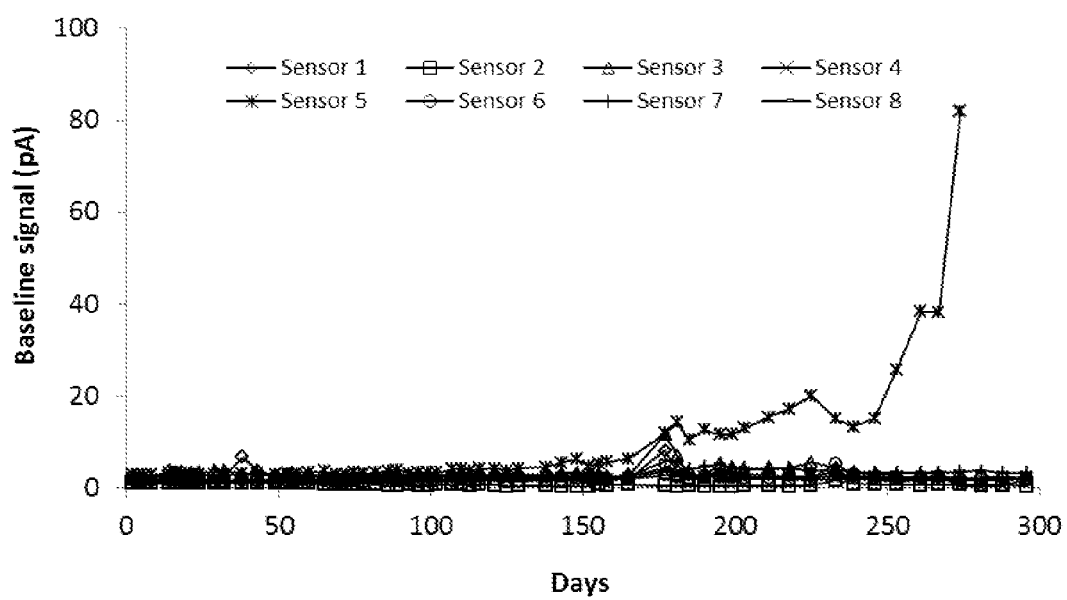
FIG. 30 shows sensor baseline signal as a function of time for sensors constructed with a secondary opening membrane length of 150 μm.

FIG. 30 shows sensor baseline signal as a function of time for sensors constructed with a secondary opening membrane length of 150 μm.

It is understood that in certain embodiments, the sensor may comprise a primary and secondary chamber which are made of a brittle material, such as relatively thin glass, and the primary and secondary chambers are enclosed by the inner tubing, which may be a polymeric material, which may be slightly elastic so as to form a tight fit around the primary and secondary chambers, without breaking the glass. The inner tubing may be enclosed by the rigid cover, such as outer tubing, which may be held in place using O-rings. In an exemplary embodiment, the complete sensor comprising inner and outer tubing, may be only 26.5 cm long and 4 cm wide (in diameter), thus forming a very compact, yet robust, sensor.

To sum up, there is presented an electrochemical sensor (100) for sensing nitrous oxide (N2O) in an associated volume (106), the sensor comprising a primary chamber (110), a secondary chamber (120) being placed adjacent the primary chamber (110), the secondary chamber (120) comprising electrodes for performing electrochemical measurements and furthermore an electrolyte comprising an aprotic solvent. A first membrane (114) and a secondary membrane (124) are permeable to nitrous oxide and may be arranged so as to separate the associated volume (106) from a primary volume (116) within the primary chamber (110), and the primary volume (116) from a secondary volume (126) within the secondary chamber (120), where the primary chamber (110) comprises means for hindering oxygen in passing into the secondary volume (126), and wherein the working electrode (104) comprises indium (In).

In embodiments E1-E21 of the invention, there is presented:

E1. An electrochemical sensor (100) for sensing nitrous oxide ($N_2O$) in an associated volume (106), the sensor comprising
a primary chamber (110) having a primary opening (112) towards the associated volume (106),
a secondary chamber (120) being placed adjacent the primary chamber (110) or partially surrounded by the primary chamber (110), the secondary chamber (120) comprising,
A working electrode (104),
A reference electrode (108), and
An electrolyte comprising an aprotic solvent,
where the secondary chamber (120) has a secondary opening (122) towards the primary chamber (110), where a secondary membrane (124) is placed in the secondary opening (122),
wherein the secondary membrane (124) is permeable to nitrous oxide and is arranged so as to separate a primary volume (116) from a secondary volume (126), said secondary volume being within the secondary chamber (120), said primary volume being within the primary chamber (110),
where the primary chamber (110) comprises means for hindering oxygen in passing into the secondary volume (126), and
wherein the working electrode (104) comprises indium (In).

E2. An electrochemical sensor according to any of the preceding embodiments, wherein the sensor comprises
a primary chamber (110) having a primary opening (112) towards the associated volume (106), where a primary membrane (114) is placed in the primary opening,
a secondary chamber (120) being placed adjacent the primary chamber (110) or partially surrounded by the primary chamber (110), the secondary chamber (120) comprising,
A working electrode (104),
A reference electrode (108), and
An electrolyte comprising an aprotic solvent,
where the secondary chamber (120) has a secondary opening (122) towards the primary chamber (110), where a secondary membrane (124) is placed in the secondary opening (122),
wherein the primary membrane (114) is permeable to nitrous oxide and is arranged so as to separate the associated volume (106) from a primary volume (116), said primary volume being within the primary chamber (110), and
wherein the secondary membrane (124) is permeable to nitrous oxide and is arranged so as to separate the primary volume (116) from a secondary volume (126), said secondary volume being within the secondary chamber (120),
where the primary chamber (110) comprises means for hindering oxygen in passing into the secondary volume (126), and
wherein the working electrode (104) comprises indium (In).

E3. An electrochemical sensor according to any of the preceding embodiments,
wherein the aprotic solvent is propylene carbonate,
wherein the means for hindering oxygen in passing into the secondary volume (126) comprises ascorbate, and
wherein an ionic compound is dissolved in the electrolyte, the ionic compound being chosen from the group comprising:
tetrabutylammonium iodide (TBA-I),
tetrabutylammonium chlorate (TBA-Cl),
tetrabutylammonium flouroborate (TBA-$BF_4$) and/or
tetrabutylammonium perchlorate (TBA-$ClO_4$).

E4. An electrochemical sensor according to any of the preceding embodiments, wherein a detection limit in liquid is less than 100 nM.

E5. An electrochemical sensor according to any of the preceding embodiments, wherein a detection limit in gas is 1 ppm or less.

E6. An electrochemical sensor according to any of the preceding embodiments, wherein a ratio between a sensor response and a baseline signal is at least 10 (pA/100 micromolar $N_2O$)/(pA).

E7. An electrochemical sensor according to any of the preceding embodiments, wherein the sensor response and/or the baseline signal is substantially stable over extended periods of time.

E8. An electrochemical sensor according to any of the preceding embodiments, wherein the aprotic solvent is propylene carbonate.

E9. An electrochemical sensor according to any of the preceding embodiments, wherein the means for hindering oxygen in passing into the secondary volume (126) comprises an oxygen scavenger.

E10. An electrochemical sensor according to any of the preceding embodiments, wherein means for hindering oxygen in passing into the secondary volume (126) comprises ascorbate.

E11. An electrochemical sensor according to any of the preceding embodiments, wherein the primary chamber has a volume of at least 0.5 milliliter.

E12. An electrochemical sensor according to any of the preceding embodiments, wherein an ionic compound is dissolved in the electrolyte, the ionic compound comprising tetrabutylammonium.

E13. An electrochemical sensor according to any of the preceding embodiments, wherein an ionic compound is dissolved in the electrolyte, the ionic compound being chosen from the group comprising
tetrabutylammonium iodide (TBA-I),
tetrabutylammonium chlorate (TBA-CI),
tetrabutylammonium flouroborate (TBA-BF$_4$) and/or
tetrabutylammonium perchlorate (TBA-ClO4).

E14. An electrochemical sensor according to any of the preceding embodiments, wherein the sensor is suited for measuring in any one of:
a gas,
a liquid.

E15. An electrochemical sensor according to any of the preceding embodiments, wherein the sensor further comprises a rigid cover (232) serving to protect the sensor.

E16. An electrochemical sensor according to any of the preceding embodiments, wherein the sensor comprises means (236) for enabling temperature compensation.

E17. An electrochemical sensor according to embodiment E16, wherein the sensor comprises means (236) for enabling temperature compensation, wherein the means for enabling temperature compensation comprises electronically stored information which enables compensating for the effects of temperature.

E18. A sensor system comprising the sensor according to any of the preceding embodiments, and further comprising
a voltage generating means for holding the working electrode at a first voltage with respect to the reference electrode, such that nitrous oxide may be reduced at the working electrode causing a current to flow through the electrode,
a current sensing means for sensing the presence of the current.

E19. A method (440) for electrochemically sensing nitrous oxide (N2O) in an associated volume, the method comprising
providing (s442) a primary chamber having a primary opening towards the associated volume,
providing (s444) a secondary chamber being placed adjacent the primary chamber or partially surrounded by the primary chamber, the secondary chamber comprising,
A working electrode (104),
A reference electrode (108), and
An electrolyte comprising an aprotic solvent,
where the secondary chamber has a secondary opening towards the primary chamber, where a secondary membrane is placed in the secondary opening,
wherein the secondary membrane (124) is permeable to nitrous oxide and is arranged so as to separate a primary volume (116) from a secondary volume (126), said secondary volume being within the secondary chamber (120), said primary volume being within the primary chamber (110), where the primary chamber (110) comprises means for hindering oxygen in passing into the secondary volume (126), and
wherein the working electrode comprises indium (In), the method further comprising reducing (s446) the nitrous oxide at the working electrode and measuring (s448) the corresponding current flowing through the working electrode.

E20. A method according to embodiment E19, the method comprising
providing (s442) a primary chamber having a primary opening towards the associated volume, where a primary membrane is placed the primary opening,
providing (s444) a secondary chamber being placed adjacent the primary chamber or partially surrounded by the primary chamber, the secondary chamber comprising,
A working electrode (104),
A reference electrode (108), and
An electrolyte comprising an aprotic solvent,
where the secondary chamber has a secondary opening towards the primary chamber, where a secondary membrane is placed in the secondary opening,
wherein the primary membrane (114) is permeable to nitrous oxide and is arranged so as to separate the associated volume (106) from a primary volume (116), said primary volume being within the primary chamber (110), and
wherein the secondary membrane (124) is permeable to nitrous oxide and is arranged so as to separate the primary volume (116) from a secondary volume (126), said secondary volume being within the secondary chamber (120),
where the primary chamber (110) comprises means for hindering oxygen in passing into the secondary volume (126), and
wherein the working electrode comprises indium (In), the method further comprising reducing (s446) the nitrous oxide at the working electrode and measuring (s448) the corresponding current flowing through the working electrode.

E21. Use of a sensor according to any one of embodiments E1-E18 for sensing the presence of nitrous oxide in an associated volume.

For the above embodiments E1-E21, it may be understood that reference to preceding 'embodiments' may refer to preceding embodiments within embodiments E1-E21.

In alternative embodiments F1-F37, there is presented (where reference signs refer to analogous features for an exemplary electrochemical sensor as described in the figures):

F1. An electrochemical sensor (100) for sensing an analyte, such as a gaseous analyte, such as nitrous oxide (N$_2$O), in an associated volume (106), the sensor comprising a primary chamber (110) having a primary opening (112) towards the associated volume (106), a secondary chamber (120) being placed adjacent the primary chamber (110) or partially surrounded by the primary chamber (110), the secondary chamber (120) comprising, A working electrode (104), A reference electrode (108), and An electrolyte comprising an aprotic solvent, where the secondary chamber (120) has a secondary opening (122) towards the primary chamber (110), where a secondary opening membrane (124) is placed in the secondary opening (122), wherein the secondary opening membrane (124) is permeable to the analyte, such as nitrous oxide, and is arranged so as to separate a primary volume (116) from a secondary volume (126), said secondary volume being within the secondary chamber (120), said primary volume being within the primary chamber (110), and wherein a secondary opening membrane length (L), said secondary opening membrane length being a length of the secondary opening membrane in a direction from the primary chamber to the secondary chamber through the secondary opening membrane, is longer than 25 micrometer, such as 30 micrometer or longer, such as 35 micrometer or longer, such as 40 micrometer or longer, such as 45 micrometer or longer, such as 50 micrometer or longer, such as 60 micrometer or longer, such as 70 micrometer or longer, such as 80 micrometer or longer, such as 90 micrometer or longer, such as 100 micrometer or longer, such as 110 micrometer or longer, such as 120 micrometer or longer, such as 130 micrometer or longer, such as 140 micrometer or longer, such as 150 micrometer or longer.

F2. An electrochemical sensor according to any of the preceding embodiments, wherein a secondary opening membrane length (L), said secondary opening membrane length being a length of the secondary opening membrane in a direction from the primary chamber to the secondary chamber through the secondary opening membrane, is 10 centimeter or shorter, such as 5 centimeter or shorter, such as 1 centimeter or shorter, such as 2 millimeter or shorter, such as 1 millimeter or shorter, such as 0.5 millimeter or shorter, such as 250 micrometer or shorter, such as 200 micrometer or shorter.

F3. An electrochemical sensor according to any of the preceding embodiments, wherein the sensor comprises a primary chamber (110) having a primary opening (112) towards the associated volume (106), where a primary membrane (114) is placed in the primary opening, a secondary chamber (120) being placed adjacent the primary chamber (110) or partially surrounded by the primary chamber (110), the secondary chamber (120) comprising, A working electrode (104), A reference electrode (108), and An electrolyte comprising an aprotic solvent, where the secondary chamber (120) has a secondary opening (122) towards the primary chamber (110), where a secondary opening membrane (124) is placed in the secondary opening (122), wherein the primary membrane (114) is permeable to the analyte and is arranged so as to separate the associated volume (106) from a primary volume (116), said primary volume being within the primary chamber (110), and wherein the secondary opening membrane (124) is permeable to the analyte and is arranged so as to separate the primary volume (116) from a secondary volume (126), said secondary volume being within the secondary chamber (120).

F4. An electrochemical sensor according to any of the preceding embodiments, wherein the working electrode (104) comprises indium (In).

F5. An electrochemical sensor according to any of the preceding embodiments, wherein the working electrode (104) comprises any one of: indium (In), platinum (Pt), gold (Au), silver (Ag), palladium (Pd), iridium (Ir) and/or carbon.

F6. An electrochemical sensor according to any of the preceding embodiments, wherein the analyte is chosen from the group of analytes wherein a polarization level applied for the sensor, such for the electrochemical sensor which is constructed with a specific combination of electrolyte and working electrode material, in order to sense the analyte is a polarization level where active water splitting takes place, such as where active water splitting takes place to a degree which degrades sensor performance, such as which under practical circumstances degrades sensor performance.

F7. An electrochemical sensor according to any of the preceding embodiments, wherein the analyte is nitrous oxide ($N_2O$).

F8. An electrochemical sensor according to any of the preceding embodiments, wherein the analyte is any one of nitrous oxide ($N_2O$), carbon dioxide ($CO_2$) and/or hydrogen ($H_2$), nitric oxide (NO), methane ($CH_4$) and/or nitrogen ($N_2$).

F9. An electrochemical sensor according to any of the preceding embodiments, where the primary chamber (110) comprises means for hindering oxygen in passing into the secondary volume (126).

F10. An electrochemical sensor according to any of the preceding embodiments, wherein the aprotic solvent is propylene carbonate, wherein the means for hindering oxygen in passing into the secondary volume (126) comprises ascorbate, and wherein an ionic compound is dissolved in the electrolyte, the ionic compound being chosen from the group comprising:

tetrabutylammonium iodide (TBA-I), tetrabutylammonium chlorate (TBA-Cl), tetrabutylammonium flouroborate (TBA-$BF_4$) and/or tetrabutylammonium perchlorate (TBA-$ClO_4$).

F11. An electrochemical sensor according to any of the preceding embodiments, wherein a secondary opening membrane length (L), said secondary opening membrane length being a length of the secondary opening membrane in a direction from the primary chamber to the secondary chamber through the secondary opening membrane, is longer than 25 micrometer.

F12. An electrochemical sensor according to any of the preceding embodiments, wherein a secondary opening membrane length (L), said secondary opening membrane length being a length of the secondary opening membrane in a direction from the primary chamber to the secondary chamber through the secondary opening membrane, is 50 micrometer or longer.

F13. An electrochemical sensor according to any of the preceding embodiments, wherein a secondary opening membrane length (L), said secondary opening membrane length being a length of the secondary opening membrane in a direction from the primary chamber to the secondary chamber through the secondary opening membrane, is 100 micrometer or longer.

F14. An electrochemical sensor according to any of the preceding embodiments, wherein a secondary opening membrane length (L), said secondary opening membrane length being a length of the secondary opening membrane in a direction from the primary chamber to the secondary chamber through the secondary opening membrane, is 5 millimeter or shorter.

F15. An electrochemical sensor according to any of the preceding embodiments, wherein a detection limit in liquid is less than 100 nM.

F16. An electrochemical sensor according to any of the preceding embodiments, wherein a detection limit in gas is 1 ppm or less.

F17. An electrochemical sensor according to any of the preceding embodiments, wherein a ratio between a sensor response and a baseline signal is at least 10 (pA/100 micromolar $N_2O$)/(pA).

F18. An electrochemical sensor according to any of the preceding embodiments, wherein the sensor response and/or the baseline signal is substantially stable over extended periods of time.

F19. An electrochemical sensor according to any of the preceding embodiments, wherein the aprotic solvent is propylene carbonate.

F20. An electrochemical sensor according to any of the preceding embodiments, wherein the means for hindering oxygen in passing into the secondary volume (126) comprises an oxygen scavenger.

F21. An electrochemical sensor according to any of the preceding embodiments, wherein means for hindering oxygen in passing into the secondary volume (126) comprises ascorbate.

F22. An electrochemical sensor according to any of the preceding embodiments, wherein the primary chamber has a volume of at least 0.5 milliliter.

F23. An electrochemical sensor according to any of the preceding embodiments, wherein an ionic compound is dissolved in the electrolyte, the ionic compound comprising tetrabutylammonium.

F24. An electrochemical sensor according to any of the preceding embodiments, wherein an ionic compound is dissolved in the electrolyte, the ionic compound being chosen from the group comprising
tetrabutylammonium iodide (TBA-I),
tetrabutylammonium chlorate (TBA-CI),
tetrabutylammonium flouroborate (TBA-$BF_4$) and/or
tetrabutylammonium perchlorate (TBA-ClO4).

F25. An electrochemical sensor according to any of the preceding embodiments, wherein the sensor is suited for measuring in any one of:
a gas,
a liquid.

F26. An electrochemical sensor according to any of the preceding embodiments, wherein the sensor further comprises a rigid cover (232) serving to protect the sensor.

F27. An electrochemical sensor according to any of the preceding embodiments, wherein the sensor comprises means (236) for enabling temperature compensation.

F28. An electrochemical sensor according to embodiment F27, wherein the sensor comprises means (236) for enabling temperature compensation, wherein the means for enabling temperature compensation comprises electronically stored information which enables compensating for the effects of temperature.

F29. A sensor system comprising the sensor according to any of the preceding embodiments, and further comprising
a voltage generating means for holding the working electrode at a first voltage with respect to the reference electrode, such that the analyte may be reduced at the working electrode causing a current to flow through the electrode,
a current sensing means for sensing the presence of the current.

F30. A method (440) for electrochemically sensing an analyte, such as a gaseous analyte, such as nitrous oxide (N2O), in an associated volume, the method comprising
providing (s442) a primary chamber having a primary opening towards the associated volume,
providing (s444) a secondary chamber being placed adjacent the primary chamber or partially surrounded by the primary chamber, the secondary chamber comprising,
A working electrode (104),
A reference electrode (108), and
An electrolyte comprising an aprotic solvent,
where the secondary chamber has a secondary opening towards the primary chamber, where a secondary opening membrane is placed in the secondary opening,
wherein the secondary opening membrane (124) is permeable to the analyte and is arranged so as to separate a primary volume (116) from a secondary volume (126), said secondary volume being within the secondary chamber (120), said primary volume being within the primary chamber (110),
the method further comprising reducing (s446) the analyte at the working electrode and measuring (s448) the corresponding current flowing through the working electrode, and wherein a secondary opening membrane length (L), said secondary opening membrane length being a length of the secondary opening membrane in a direction from the primary chamber to the secondary chamber through the secondary opening membrane, is longer than 25 micrometer, such as 30 micrometer or longer, such as 35 micrometer or longer, such as 40 micrometer or longer, such as 45 micrometer or longer, such as 50 micrometer or longer, such as 60 micrometer or longer, such as 70 micrometer or longer, such as 80 micrometer or longer, such as 90 micrometer or longer, such as 100 micrometer or longer, such as 110 micrometer or longer, such as 120 micrometer or longer, such as 130 micrometer or longer, such as 140 micrometer or longer, such as 150 micrometer or longer.

F31. A method (440) for electrochemically sensing an analyte in an associated volume according to embodiment F30, wherein a secondary opening membrane length (L), said secondary opening membrane length being a length of the secondary opening membrane in a direction from the primary chamber to the secondary chamber through the secondary opening membrane, is 10 centimeter or shorter, such as 5 centimeter or shorter, such as 1 centimeter or shorter, such as 2 millimeter or shorter, such as 1 millimeter or shorter, such as 0.5 millimeter or shorter, such as 250 micrometer or shorter, such as 200 micrometer or shorter.

F32. A method according to any one of embodiments F30-F31, the method comprising providing (s442) a primary chamber having a primary opening towards the associated volume, where a primary membrane is placed the primary opening, providing (s444) a secondary chamber being placed adjacent the primary chamber or partially surrounded by the primary chamber, the secondary chamber comprising, A working electrode (104), A reference electrode (108), and An electrolyte comprising an aprotic solvent, where the secondary chamber has a secondary opening towards the primary chamber, where a secondary opening membrane is placed in the secondary opening, wherein the primary membrane (114) is permeable to the analyte and is arranged so as to separate the associated volume (106) from a primary volume (116), said primary volume being within the primary chamber (110), and wherein the secondary opening membrane (124) is permeable to the analyte and is arranged so as to separate the primary volume (116) from a secondary volume (126), said secondary volume being within the secondary chamber (120), where the primary chamber (110) comprises means for hindering oxygen in passing into the secondary volume (126, the method further comprising reducing (s446) the analyte at the working electrode and measuring (s448) the corresponding current flowing through the working electrode.

F33. A method (440) for electrochemically sensing an analyte in an associated volume according to any one of embodiments F30-F32, wherein the working electrode (104) any one of: indium (In), platinum (Pt), gold (Au), silver (Ag), palladium (Pd), iridium (Ir) and/or carbon.

F34. A method (440) for electrochemically sensing an analyte according to any one of embodiments F30-F33, wherein the analyte is chosen from the group of analytes wherein a polarization level applied for the sensor, such for the electrochemical sensor which is constructed with a specific combination of electrolyte and working electrode material, in order to sense the analyte is a polarization level where active water splitting takes place, such as where active water splitting takes place to a degree which degrades sensor performance, such as which under practical circumstances degrades sensor performance.

F35. A method (440) for electrochemically sensing an analyte according to any one of embodiments F30-F34, wherein the analyte is any one of nitrous oxide ($N_2O$), carbon dioxide ($CO_2$) and/or hydrogen ($H_2$), nitric oxide (NO), methane ($CH_4$) and/or nitrogen ($N_2$).

F36. A method (440) for electrochemically sensing an analyte according to any one of embodiments F30-F35, where the primary chamber (110) comprises means for hindering oxygen in passing into the secondary volume (126)

F37. Use of a sensor according to any one of embodiments F1-F29 for sensing the presence of an analyte, such as nitrous oxide, in an associated volume.

For the above embodiments F1-F37, it may be understood that reference to preceding 'embodiments' may refer to preceding embodiments within embodiments F1-F37. For the above embodiments F1-F37, it may be understood that for certain analytes, such as $H_2$, the primary chamber may be dispensed with.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An electrochemical sensor for sensing nitrous oxide ($N_2O$) in an associated volume, the sensor comprising:

a primary chamber having a primary opening towards the associated volume, a secondary chamber being placed adjacent the primary chamber or partially surrounded by the primary chamber, the secondary chamber comprising, A working electrode, A reference electrode, and An electrolyte comprising an aprotic solvent, where the secondary chamber has a secondary opening towards the primary chamber, where a secondary opening membrane is placed in the secondary opening, wherein the secondary opening membrane is permeable to nitrous oxide and is arranged so as to separate a primary volume from a secondary volume, said secondary volume being within the secondary chamber, said primary volume being within the primary chamber, where the primary chamber comprises a chemically active entity, which degrades oxygen, or a selective barrier that is impermeable to oxygen, and wherein the working electrode comprises indium (In) as a reactive surface component and said working electrode is configured such that the catalytic properties of the element indium towards reduction of nitrous oxide may be utilized.

2. The electrochemical sensor according to claim 1, wherein a secondary opening membrane length, said secondary opening membrane length being a length of the secondary opening membrane in a direction from the primary chamber to the secondary chamber through the secondary opening membrane, is longer than 25 micrometer.

3. The electrochemical sensor according to claim 1, wherein a secondary opening membrane length, said secondary opening membrane length being a length of the secondary opening membrane in a direction from the primary chamber to the secondary chamber through the secondary opening membrane, is 50 micrometer or longer.

4. The electrochemical sensor according to claim 1, wherein a secondary opening membrane length, said secondary opening membrane length being a length of the secondary opening membrane in a direction from the primary chamber to the secondary chamber through the secondary opening membrane, is 100 micrometer or longer.

5. The electrochemical sensor according to claim 1, wherein a secondary opening membrane length, said secondary opening membrane length being a length of the secondary opening membrane in a direction from the primary chamber to the secondary chamber through the secondary opening membrane, is 5 millimeter or shorter.

6. The electrochemical sensor according to claim 1, wherein a primary membrane is placed in the primary opening and wherein the primary membrane is permeable to nitrous oxide and is arranged so as to separate the associated volume from a primary volume, said primary volume being within the primary chamber.

7. The electrochemical sensor according to claim 1, wherein the aprotic solvent is propylene carbonate,
wherein the chemically active entity, which degrades oxygen, or the selective barrier that is impermeable to oxygen comprises ascorbate, and
wherein an ionic compound is dissolved in the electrolyte, the ionic compound being:
tetrabutylammonium iodide (TBA-I),
tetrabutylammonium chlorate (TBA-Cl),
tetrabutylammonium flouroborate (TBA-$BF_4$) and/or
tetrabutylammonium perchlorate (TBA-$ClO_4$).

8. The electrochemical sensor according to claim 1, wherein the aprotic solvent is propylene carbonate.

9. The electrochemical sensor according to claim 1, wherein the chemically active entity, which degrades oxygen, or the selective barrier that is impermeable to oxygen comprises an oxygen scavenger.

10. The electrochemical sensor according to claim 1, wherein the chemically active entity, which degrades oxygen, or the selective barrier that is impermeable to oxygen comprises ascorbate.

11. The electrochemical sensor according to claim 1, wherein the primary chamber has a volume of at least 0.5 milliliter.

12. The electrochemical sensor according to claim 1, wherein an ionic compound is dissolved in the electrolyte, the ionic compound comprising tetrabutylammonium.

13. The electrochemical sensor according to claim 1, wherein an ionic compound is dissolved in the electrolyte, the ionic compound being:
tetrabutylammonium iodide (TBA-I),
tetrabutylammonium chlorate (TBA-Cl),
tetrabutylammonium flouroborate (TBA-$BF_4$) and/or tetrabutylammonium perchlorate (TBA-ClO4).

14. The electrochemical sensor according to claim 1, wherein the sensor further comprises a rigid cover serving to protect the sensor.

15. The electrochemical sensor according to claim 1, wherein the sensor comprises electronically stored information, which is descriptive of the influence of temperature on the output of the sensor.

16. A sensor system comprising the sensor according to claim 1, and further comprising:
a potentiostat for holding the working electrode at a first voltage with respect to the reference electrode, such that nitrous oxide may be reduced at the working electrode causing a current to flow through the electrode, and
an ammeter for sensing the presence of the current.

17. A method for electrochemically sensing nitrous oxide (N2O) in an associated volume, the method comprising:
providing a primary chamber having a primary opening towards the associated volume,
providing a secondary chamber being placed adjacent the primary chamber or partially surrounded by the primary chamber, the secondary chamber comprising,
A working electrode,
A reference electrode, and
An electrolyte comprising an aprotic solvent,
where the secondary chamber has a secondary opening towards the primary chamber, where a secondary opening membrane is placed in the secondary opening,
wherein the secondary opening membrane is permeable to nitrous oxide and is arranged so as to separate a primary volume from a secondary volume, said secondary volume being within the secondary chamber, said primary volume being within the primary chamber,
where the primary chamber comprises a chemically active entity, which degrades oxygen, or a selective barrier that is impermeable to oxygen, and
wherein the working electrode comprises indium (In) as a reactive surface component and said working electrode is configured such that the catalytic properties of the element indium towards reduction of nitrous oxide may be utilized, the method further comprising reducing the nitrous oxide at the working electrode and measuring the corresponding current flowing through the working electrode.

18. The method according to claim 17, wherein a primary membrane is placed in the primary opening and wherein the primary membrane is permeable to nitrous oxide and is arranged so as to separate the associated volume from a primary volume, said primary volume being within the primary chamber.

19. A method of using the sensor of claim 1 for sensing the presence of nitrous oxide in sample comprising:
contacting a sample with the sensor of claim 1; and
detecting the presence or absence of nitrous oxide in said sample.

* * * * *